United States Patent [19]

Ouchi

[11] Patent Number: 5,788,714
[45] Date of Patent: Aug. 4, 1998

[54] FLEXIBLE TUBE FOR AN ENDOSCOPE

[75] Inventor: Teruo Ouchi, Tokyo, Japan

[73] Assignee: Asahi Kogaku Kogyo Kabushiki Kaisha, Tokyo, Japan

[21] Appl. No.: 694,499

[22] Filed: Aug. 7, 1996

[30] Foreign Application Priority Data

| Aug. 14, 1995 | [JP] | Japan | 7-206878 |
|---|---|---|---|
| Aug. 14, 1995 | [JP] | Japan | 7-206879 |
| Aug. 24, 1995 | [JP] | Japan | 7-215780 |
| Aug. 24, 1995 | [JP] | Japan | 7-215781 |
| Aug. 24, 1995 | [JP] | Japan | 7-215782 |
| Aug. 24, 1995 | [JP] | Japan | 7-215783 |

[51] Int. Cl.⁶ ............................................. A61B 1/00
[52] U.S. Cl. .................... 600/140; 600/139; 138/123
[58] Field of Search ............................. 600/139, 140, 600/142, 143, 144, 920; 138/118, 123, 124, 127

[56] References Cited

U.S. PATENT DOCUMENTS 4,495,134  1/1985  Ouchi et al. .
4,690,175  9/1987  Ouchi et al. .

FOREIGN PATENT DOCUMENTS

| 4929109 | 2/1969 | Japan . |
|---|---|---|
| 62133925 | 12/1985 | Japan . |
| 1104234 | 10/1987 | Japan . |
| 1232923 | 9/1989 | Japan . |
| 2-46207 | 10/1990 | Japan . |
| 3-29406 | 4/1991 | Japan . |
| 3-42896 | 6/1991 | Japan . |
| 3-58725 | 9/1991 | Japan . |
| 5-19043 | 5/1993 | Japan . |

*Primary Examiner*—Beverly M. Flanagan
*Attorney, Agent, or Firm*—Kane, Dalsimer, Sullivan, Kurucz, Levy, Eisele and Richard, LLP

[57] ABSTRACT

A flexible tube for an endoscope that includes a spiral tube, a netted tube that covers the outer surface of the spiral tube, and a jacket. The netted tube is formed by braiding a plurality of strand bundles each formed by closely arranging a plurality of fine wires in parallel. The jacket is made of a flexible synthetic resin which covers the outer surface of the netted tube. The braid density K of the netted tube lies in a range of $0.772 \leq K \leq 0.906$.

68 Claims, 36 Drawing Sheets

| | ① | ② | ③ | ④ | ⑤ |
|---|---|---|---|---|---|
| OUTER DIAMETER OF FLEXIBLE TUBE (mm) | 12.76 | ↓ | ↓ | ↓ | ↓ |
| OUTER DIAMETER OF NETTED TUBE (mm) | 11.76 | ↓ | ↓ | ↓ | ↓ |
| OUTER DIAMETER OF SPIRAL TUBE (mm) | 11.36 | ↓ | ↓ | ↓ | ↓ |
| THICKNESS OF FLEXIBLE JACKET (mm) | 0.5 | ↓ | ↓ | ↓ | ↓ |
| AVERAGE DIAMETER OF NETTED TUBE (mm) | 11.56 | ↓ | ↓ | ↓ | ↓ |
| DIAMETER OF EACH STRAND IN STRAND BUNDLE (mm) × n | 0.1 × 6 | 0.1 × 7 | 0.1 × 8 | 0.1 × 9 | 0.1 × 10 |
| m | 32 | ↓ | ↓ | ↓ | ↓ |
| BRAID PITCH (mm) | 25 | ↓ | ↓ | ↓ | ↓ |
| BRAID ANGLE α (CALCULATED VALUE) | 55.4° | ↓ | ↓ | ↓ | ↓ |
| BRAID DENSITY K | 0.715 | 0.792 | 0.857 | 0.91 | 0.951 |

FIG. 4A

| EVALUATION | | ACCEPTABLE (1.2 kg or more) | ACCEPTABLE (0.8 kg-1.2kg) | ACCEPTABLE (0.8kg-1.0kg) | RATHER UNACCEPTABLE (0.6kg-0.8kg) | UNACCEPTABLE (0.4kg-0.6kg) |
|---|---|---|---|---|---|---|
| | BONDING WITH NETTED TUBE (PEELING STRENGTH) | | | | | |
| | BONDING WITH NETTED TUBE (PEELING STRENGTH) | MUCH OF THE FLEXIBLE JACKET MATERIAL BULGES INTO THE SPIRAL TUBE, AND IS INTEGRATED WITH THE NETTED TUBE | FLEXIBLE JACKET MATERIAL COLLECTS AT THE BOTTOM OF THE NETTED TUBE | FLEXIBLE JACKET MATERIAL COLLECTS WITHIN THE WALL THICKNESS OF THE NETTED TUBE | FLEXIBLE JACKET MATERIAL SLIGHTLY PENETRATES INTO THE NETTED TUBE | FLEXIBLE JACKET MATERIAL COLLECTS IN THE BONDING SECTION WITH THE SURFACE OF THE NETTED TUBE |
| | PENETRATION INTO NETTED TUBE | HIGH | HIGH | MEDIUM | LOW | VERY LOW |
| | PENETRATION INTO SPIRAL TUBE | HIGH | NONE | NONE | NONE | NONE |

| | ① | ② | ③ | ④ | ⑤ |
|---|---|---|---|---|---|
| OUTER DIAMETER OF FLEXIBLE TUBE (mm) | 9.02 | ↓ | ↓ | ↓ | ↓ |
| OUTER DIAMETER OF NETTED TUBE (mm) | 8.22 | ↓ | ↓ | ↓ | ↓ |
| OUTER DIAMETER OF SPIRAL TUBE (mm) | 7.9 | ↓ | ↓ | ↓ | ↓ |
| THICKNESS OF FLEXIBLE JACKET (mm) | 0.4 | ↓ | ↓ | ↓ | ↓ |
| AVERAGE DIAMETER OF NETTED TUBE (mm) | 8.06 | ↓ | ↓ | ↓ | ↓ |
| DIAMETER OF EACH STRAND IN STRAND BUNDLE (mm × n) | 0.08 × 6 | 0.08 × 7 | 0.08 × 8 | 0.08 × 9 | 0.08 × 10 |
| m | 32 | ↓ | ↓ | ↓ | ↓ |
| BRAID PITCH (mm) | 22 | ↓ | ↓ | ↓ | ↓ |
| BRAID ANGLE α (CALCULATED VALUE) | 49° | ↓ | ↓ | ↓ | ↓ |
| BRAID DENSITY K | 0.711 | 0.788 | 0.853 | 0.906 | 0.948 |
| EVALUATION — PENETRATION INTO NETTED TUBE | HIGH | HIGH | MEDIUM | LOW | VERY LOW |
| EVALUATION — PENETRATION INTO SPIRAL TUBE | HIGH | NONE | NONE | NONE | NONE |
| EVALUATION — BONDING WITH NETTED TUBE | HIGH | HIGH | HIGH | MEDIUM | VERY LOW |

| | ① | ② | ③ | ④ | ⑤ |
|---|---|---|---|---|---|
| OUTER DIAMETER OF FLEXIBLE TUBE (mm) | 5.06 | ↓ | ↓ | ↓ | ↓ |
| OUTER DIAMETER OF NETTED TUBE (mm) | 4.66 | ↓ | ↓ | ↓ | ↓ |
| OUTER DIAMETER OF SPIRAL TUBE (mm) | 4.46 | ↓ | ↓ | ↓ | ↓ |
| THICKNESS OF FLEXIBLE JACKET (mm) | 0.2 | ↓ | ↓ | ↓ | ↓ |
| AVERAGE DIAMETER OF NETTED TUBE (mm) | 4.56 | ↓ | ↓ | ↓ | ↓ |
| DIAMETER OF EACH STRAND IN STRAND BUNDLE (mm) × n | 0.05 × 7 | 0.05 × 8 | 0.05 × 9 | 0.05 × 10 | 0.05 × 11 |
| m | 24 | ↓ | ↓ | ↓ | ↓ |
| BRAID PITCH (mm) | 22 | ↓ | ↓ | ↓ | ↓ |
| BRAID ANGLE α (CALCULATED VALUE) | 50° | ↓ | ↓ | ↓ | ↓ |
| BRAID DENSITY K | 0.705 | 0.772 | 0.83 | 0.879 | 0.92 |
| EVALUATION – PENETRATION INTO NETTED TUBE | HIGH | HIGH | MEDIUM | MEDIUM | VERY LOW |
| EVALUATION – PENETRATION INTO SPIRAL TUBE | HIGH | VERY LOW | NONE | NONE | NONE |
| EVALUATION – BONDING WITH NETTED TUBE | ACCEPTABLE | ACCEPTABLE | ACCEPTABLE | RATNER UNACCEPTABLE | UNACCEPTABLE |

| | ① | ② | ③ | ④ | ⑤ | ⑥ |
|---|---|---|---|---|---|---|
| OUTER DIAMETER OF FLEXIBLE TUBE (mm) | 3.58 | ↓ | ↓ | ↓ | ↓ | ↓ |
| OUTER DIAMETER OF NETTED TUBE (mm) | 3.22 | ↓ | ↓ | ↓ | ↓ | ↓ |
| OUTER DIAMETER OF SPIRAL TUBE (mm) | 3.1 | ↓ | ↓ | ↓ | ↓ | ↓ |
| THICKNESS OF FLEXIBLE JACKET (mm) | 0.18 | ↓ | ↓ | ↓ | ↓ | ↓ |
| AVERAGE DIAMETER OF NETTED TUBE (mm) | 3.16 | ↓ | ↓ | ↓ | ↓ | ↓ |
| DIAMETER OF EACH STRAND IN STRAND-BUNDLE (mm) × n | 0.03 × 9 | 0.03 × 10 | 0.03 × 11 | 0.03 × 12 | 0.03 × 13 | 0.03 × 14 |
| m | 24 | ↓ | ↓ | ↓ | ↓ | ↓ |
| BRAID PITCH (mm) | 9 | ↓ | ↓ | ↓ | ↓ | ↓ |
| BRAID ANGLE α (CALCULATED VALUE) | 47.8° | ↓ | ↓ | ↓ | ↓ | ↓ |
| BRAID DENSITY K | 0.735 | 0.788 | 0.835 | 0.876 | 0.911 | 0.94 |
| EVALUATION | PENETRATION INTO NETTED TUBE | HIGH | HIGH | MEDIUM | MEDIUM | LOW | VERY LOW |
| | PENETRATION INTO SPIRAL TUBE | LOW | NONE | NONE | NONE | NONE | NONE |
| | BONDING WITH NETTED TUBE | ACCEPTABLE | ACCEPTABLE | ACCEPTABLE | ACCEPTABLE | UNACCEPTABLE | UNACCEPTABLE |

| | ① | ② | ③ | ④ |
|---|---|---|---|---|
| OUTER DIAMETER OF FLEXIBLE TUBE (mm) | 4.248 | ← | ← | ← |
| OUTER DIAMETER OF NETTED TUBE (mm) | 3.888 | ← | ← | ← |
| OUTER DIAMETER OF SPIRAL TUBE (mm) | 3.8 | ← | ← | ← |
| THICKNESS OF FLEXIBLE JACKET (mm) | 0.18 | ← | ← | ← |
| AVERAGE DIAMETER OF NETTED TUBE (mm) | 3.844 | ← | ← | ← |
| n | 3 | 4 | 5 | 6 |
| m | 24 | ← | ← | ← |
| BRAID PITCH (mm) | 10 | ← | ← | ← |
| BRAID ANGLE α (CALCULATED VALUE) | 50.4° | ← | ← | ← |
| BRAID DENSITY K | 0.659 | 0.801 | 0.906 | 0.972 |
| EVALUATION — PENETRATION INTO NETTED TUBE | HIGH | HIGH | MEDIUM | VERY LOW |
| EVALUATION — PENETRATION INTO SPIRAL TUBE | HIGH | NONE | NONE | NONE |
| EVALUATION — BONDING WITH NETTED TUBE | HIGH | HIGH | MEDIUM | LOW |

FIG. 9

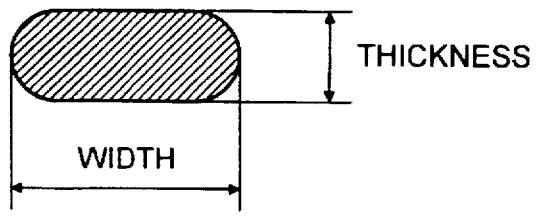

FIG. 10

| | ① | ② | ③ | ④ | ⑤ |
|---|---|---|---|---|---|
| OUTER DIAMETER OF FLEXIBLE TUBE (mm) | 12.76 | ↓ | ↓ | ↓ | ↓ |
| OUTER DIAMETER OF NETTED TUBE (mm) | 11.76 | ↓ | ↓ | ↓ | ↓ |
| OUTER DIAMETER OF SPIRAL TUBE (mm) | 11.36 | ↓ | ↓ | ↓ | ↓ |
| THICKNESS OF FLEXIBLE JACKET (mm) | 0.5 | ↓ | ↓ | ↓ | ↓ |
| AVERAGE DIAMETER OF NETTED TUBE (mm) | 11.56 | ↓ | ↓ | ↓ | ↓ |
| DIAMETER OF EACH STRAND IN STRAND BUNDLE (mm) × n (NUMBER OF METAL BRAIDS) (NUMBER OF NON-METAL BRAIDS) | 0.1 × 6 (4) (2) | 0.1 × 7 (5) (2) | 0.1 × 8 (5) (3) | 0.1 × 9 (6) (3) | 0.1 × 10 (7) (3) |
| m | 32 | ↓ | ↓ | ↓ | ↓ |
| BRAID PITCH (mm) | 25 | ↓ | ↓ | ↓ | ↓ |
| BRAID ANGLE α (CALCULATED VALUE) | 55.4° | ↓ | ↓ | ↓ | ↓ |
| BRAID DENSITY K | 0.715 | 0.792 | 0.857 | 0.91 | 0.951 |

FIG. 32A

| EVALUATION | ACCEPTABLE (1.2 kg or more) | ACCEPTABLE (0.8 kg-1.2kg) | ACCEPTABLE (0.8kg-1.0kg) | RATHER UNACCEPTABLE (0.6kg-0.8kg) | UNACCEPTABLE (0.4kg-0.6kg) |
|---|---|---|---|---|---|
| BONDING WITH NETTED TUBE (PEELING STRENGTH) | | | | | |
| BULGE INTO SPIRAL TUBE | MUCH OF THE FLEXIBLE JACKET MATERIAL BULGES INTO THE SPIRAL TUBE, AND IS INTEGRATED WITH THE NETTED TUBE | FLEXIBLE JACKET MATERIAL COLLECTS AT THE BOTTOM OF THE NETTED TUBE | FLEXIBLE JACKET MATERIAL COLLECTS WITHIN THE WALL THICKNESS OF THE NETTED TUBE | FLEXIBLE JACKET MATERIAL SLIGHTLY PENETRATES INTO THE NETTED TUBE | FLEXIBLE JACKET MATERIAL COLLECTS IN THE BONDING SECTION WITH THE SURFACE OF THE NETTED TUBE |
| PENETRATION INTO NETTED TUBE | HIGH | HIGH | MEDIUM | LOW | VERY LOW |
| PENETRATION INTO SPIRAL TUBE | HIGH | NONE | NONE | NONE | NONE |

FIG. 32B

| | ① | ② | ③ | ④ | ⑤ |
|---|---|---|---|---|---|
| OUTER DIAMETER OF FLEXIBLE TUBE (mm) | 9.02 | ↓ | ↓ | ↓ | ↓ |
| OUTER DIAMETER OF NETTED TUBE (mm) | 8.22 | ↓ | ↓ | ↓ | ↓ |
| OUTER DIAMETER OF SPIRAL TUBE (mm) | 7.9 | ↓ | ↓ | ↓ | ↓ |
| THICKNESS OF FLEXIBLE JACKET (mm) | 0.4 | ↓ | ↓ | ↓ | ↓ |
| AVERAGE DIAMETER OF NETTED TUBE (mm) | 8.06 | ↓ | ↓ | ↓ | ↓ |
| DIAMETER OF EACH STRAND IN STRAND BUNDLE (mm) x n (NUMBER OF METAL BRAIDS) (NUMBER OF NON-METAL BRAIDS) | 0.08 × 6 (4) (2) | 0.08 × 7 (5) (2) | 0.08 × 8 (6) (2) | 0.08 × 9 (7) (2) | 0.08 × 10 (7) (3) |
| m | 32 | ↓ | ↓ | ↓ | ↓ |
| BRAID PITCH (mm) | 22 | ↓ | ↓ | ↓ | ↓ |
| BRAID ANGLE α (CALCULATED VALUE) | 49° | ↓ | ↓ | ↓ | ↓ |
| BRAID DENSITY K | 0.711 | 0.788 | 0.853 | 0.906 | 0.948 |
| EVALUATION — PENETRATION INTO NETTED TUBE | HIGH | HIGH | MEDIUM | LOW | VERY LOW |
| EVALUATION — PENETRATION INTO SPIRAL TUBE | HIGH | NONE | NONE | NONE | NONE |
| EVALUATION — BONDING WITH NETTED TUBE | HIGH | HIGH | HIGH | MEDIUM | VERY LOW |

FIG. 33

| | ① | ② | ③ | ④ |
|---|---|---|---|---|
| OUTER DIAMETER OF FLEXIBLE TUBE (mm) | 6.24 | ← | ← | ← |
| OUTER DIAMETER OF NETTED TUBE (mm) | 5.64 | ← | ← | ← |
| OUTER DIAMETER OF SPIRAL TUBE (mm) | 5.32 | ← | ← | ← |
| THICKNESS OF FLEXIBLE JACKET (mm) | 0.3 | ← | ← | ← |
| AVERAGE DIAMETER OF NETTED TUBE (mm) | 5.48 | ← | ← | ← |
| DIAMETER OF EACH STRAND BUNDLE (mm) x n (NUMBER OF METAL BRAIDS) (NUMBER OF NON-METAL BRAIDS) | 0.08 x 5 (3) (2) | 0.08 x 6 (4) (2) | 0.08 x 7 (5) (2) | 0.08 x 8 (6) (2) |
| m | 24 | ← | ← | ← |
| BRAID PITCH (mm) | 12 | ← | ← | ← |
| BRAID ANGLE α (CALCULATED VALUE) | 55.1° | ← | ← | ← |
| BRAID DENSITY K | 0.738 | 0.829 | 0.90 | 0.952 |
| EVALUATION — PENETRATION INTO NETTED TUBE | HIGH | MEDIUM | LOW | UNACCEPTABLE |
| EVALUATION — PENETRATION INTO SPIRAL TUBE | MEDIUM | NONE | NONE | NONE |
| EVALUATION — BONDING WITH NETTED TUBE | HIGH | HIGH | MEDIUM | UNACCEPTABLE |

| | ① | ② | ③ | ④ | ⑤ | ⑥ |
|---|---|---|---|---|---|---|
| OUTER DIAMETER OF FLEXIBLE TUBE (mm) | 3.58 | ↓ | ↓ | ↓ | ↓ | ↓ |
| OUTER DIAMETER OF NETTED TUBE (mm) | 3.22 | ↓ | ↓ | ↓ | ↓ | ↓ |
| OUTER DIAMETER OF SPIRAL TUBE (mm) | 3.1 | ↓ | ↓ | ↓ | ↓ | ↓ |
| THICKNESS OF FLEXIBLE JACKET (mm) | 0.18 | ↓ | ↓ | ↓ | ↓ | ↓ |
| AVERAGE DIAMETER OF NETTED TUBE (mm) | 3.16 | ↓ | ↓ | ↓ | ↓ | ↓ |
| DIAMETER OF EACH STRAND IN STRAND BUNDLE (mm) × n (NUMBER OF METAL BRAIDS) (NUMBER OF NUMBER NON-METAL BRAIDS) | 0.03 × 9 (6) (3) | 0.03 × 10 (7) (3) | 0.03 × 11 (8) (3) | 0.03 × 12 (9) (3) | 0.03 × 13 (10) (3) | 0.03 × 14 (11) (3) |
| m | 24 | ↓ | ↓ | ↓ | ↓ | ↓ |
| BRAID PITCH (mm) | 9 | ↓ | ↓ | ↓ | ↓ | ↓ |
| BRAID ANGLE α (CALCULATED VALUE) | 47.8° | ↓ | ↓ | ↓ | ↓ | ↓ |
| BRAID DENSITY K | 0.735 | 0.788 | 0.835 | 0.876 | 0.911 | 0.94 |
| EVALUATION — PENETRATION INTO NETTED TUBE | HIGH | HIGH | MEDIUM | MEDIUM | LOW | VERY LOW |
| EVALUATION — PENETRATION INTO SPIRAL TUBE | HIGH | NONE | NONE | NONE | NONE | NONE |
| EVALUATION — BONDING WITH NETTED TUBE | ACCEPTABLE | ACCEPTABLE | ACCEPTABLE | ACCEPTABLE | UNACCEPTABLE | UNACCEPTABLE |

FLEXIBLE TUBE FOR AN ENDOSCOPE

BACKGROUND OF THE INVENTION

1. Field of the Invention

The present invention relates to a flexible tube used for an endoscope.

2. Description of the Related Art

A flexible tube for an endoscope is generally formed by covering an outer surface of a spiral tube with a netted tube. The netted tube is formed by braiding a plurality of strand bundles. Each of the plurality of strand bundles consists of a plurality of fine wires arranged in parallel. The outer surface of the netted tube is then covered (coated) with a flexible jacket made of a flexible synthetic resin.

For example, as disclosed in Japanese Laid-Open Patent Application No. 1-232923 and shown in FIG. 36, the ratio of the total of the length L (i.e., the combined total) of intersection between each strand bundle 21 in the axial direction of the netted tube 20 to the whole axial length of the flexible tube is arranged to be 73%–83%.

When this ratio is converted into a braid density K which is the ratio of the area of each strand bundle 21 covering the outer surface of the netted tube 20 (in FIG. 37, $K=(S-s)/S$), since $$1-(1-0.73)^2=0.9271,$$

and $$1-(1-0.83)^2=0.9711,$$

$0.927 \leq K \leq 0.971$. In addition, if there is no gap between each strand bundle 21, $s=0$, and thus $K=1$.

During use, the flexible tube for an endoscope is repeatedly bent by an amount having a small radius of curvature, in a body cavity or the like. However, since a flexible tube having a netted tube with a high braid density and a small gap between each strand bundle, as described above, has a low bonding strength between the netted tube and the flexible jacket, the flexible jacket easily detaches (separates) from the netted tube when the flexible tube is bent by an amount having a small radius of curvature, so that creases are generated in the flexible jacket on an inner side of the bent portion. In addition, buckling may occur.

To enhance bonding strength between the netted tube and the flexible jacket, if it is arranged to make the braid density of the netted tube less dense so that softened or molten flexible jacket material can sufficiently penetrate into the gaps formed in the netted tube, the flexible jacket material penetrates the netted tube up to the spiral tube (provided inside the netted tube), thus preventing the flexible tube from being smoothly bent, i.e., rendering the flexible tube useless.

SUMMARY OF THE INVENTION

An object of the present invention is to provide a flexible tube for an endoscope which has a high bonding strength between a netted tube and a jacket, and can be smoothly bent.

Another object of the present invention is to provide a netted tube, used for the aforementioned flexible tube, that realizes the above-noted high bonding strength between the netted tube and the jacket.

To achieve the former object mentioned above, according to an aspect of the present invention, there is provided a flexible tube for an endoscope that includes a spiral tube, a netted tube that covers the outer surface of the spiral tube, and a jacket. The netted tube is formed by braiding a plurality of strand bundles each formed by closely arranging a plurality of fine wires in parallel. The jacket is made of a flexible synthetic resin which covers the outer surface of the netted tube. The braid density K of the netted tube lies in a range of $0.772 \leq K \leq 0.906$.

With this arrangement, the inventor of the present invention has found that a high bonding strength can be obtained between the netted tube and the flexible jacket when the braid density K is arranged to be less than or equal to 0.906 ($K \leq 0.906$). Consequently, creases hardly occur, even if the flexible tube is bent by an amount having a small radius of curvature. Further, the inventor has found that the flexible jacket does not bind to the spiral tube when the braid density K is arranged to be greater than or equal to 0.772 ($0.772 \leq K$). Thus the flexible tube can be smoothly bent and has a good insertion capability for insertion into a body cavity.

Preferably, the jacket is formed by dissolving a synthetic resin in a solvent and applying a resultant material to the outer surface of the netted tube. However, the jacket could also be formed by heating a thermoplastic synthetic resin at a temperature higher than a softening point of the thermoplastic synthetic resin, so that the thermoplastic synthetic resin penetrates gaps formed in the netted tube from outside the netted tube.

The jacket is preferably a synthetic resin consisting of a polyurethane elastomer.

The jacket is preferably formed by firstly covering the netted tube with a synthetic resin formed in a tubular shape, and then heating the synthetic resin at a temperature higher than a softening point of the synthetic resin, so that the synthetic resin penetrates gaps formed in the netted tube from outside the netted tube.

The spiral tube is preferably made of a stainless steel or a copper alloy.

It is preferred that the plurality of fine wires are each made of metal such as a stainless steel, a copper alloy or a tungsten steel.

To achieve the latter object mentioned above, according to yet another aspect of the present invention, a netted tube, formed by braiding a plurality of strand bundles each formed by closely arranging a plurality of fine wires in parallel, is used in a flexible tube for an endoscope. The flexible tube has a spiral tube and a jacket. The netted tube covers an outer surface of the spiral tube. The jacket is made of a flexible synthetic resin which covers an outer surface of the netted tube. The following relationships are satisfied:

$$45° \leq \alpha \leq 65°,$$

$$0.772 \leq K \leq 0.906$$

and $$n=24,$$

wherein "$\alpha$" represents a braid angle, "K" represents a braid density, and "n" represents a number of strands contained in one of the plurality of strand bundles. The number "n" satisfies the following relationships:

$2.89\ D \leq n \leq 6.41\ D$ when dw is equal to 0.02 mm,
$1.93\ D \leq n \leq 4.27\ D$ when dw is equal to 0.03 mm,
$1.45\ D \leq n \leq 3.20\ D$ when dw is equal to 0.04 mm,
$1.16\ D \leq n \leq 2.56\ D$ when dw is equal to 0.05 mm, 0.97 D≦n≦2.13 D when dw is equal to 0.06 mm,
0.83 D≦n≦1.83 D when dw is equal to 0.07 mm,
0.73 D≦n≦1.60 D when dw is equal to 0.08 mm,
0.65 D≦n≦1.42 D when dw is equal to 0.09 mm,
0.58 D≦n≦1.28 D when dw is equal to 0.10 mm, and
0.49 D≦n≦1.06 D when dw is equal to 0.12 mm, wherein "dw" represents a diameter of a strand of each strand bundle in the plurality of strand bundles and "D" represents an average diameter of the netted tube.

In a further aspect of the present invention, a netted tube, formed by braiding a plurality of strand bundles each formed by closely arranging a plurality of fine wires in parallel, is used in a flexible tube for an endoscope. The flexible tube has a spiral tube and a jacket. The netted tube covers an outer surface of the spiral tube. The jacket is made of a flexible synthetic resin which covers an outer surface of the netted tube. The following relationships are satisfied:

$$45° \leq \alpha \leq 65°,$$

$$0.772 \leq K \leq 0.906$$

and $$n = 32,$$

wherein "$\alpha$" represents a braid angle, "K" represents a braid density, and "n" represents a number of strands contained in one of the plurality of strand bundles. The number "n" satisfies the following relationships:

2.17 D≦n≦4.81 D when dw is equal to 0.02 mm,
1.45 D≦n≦3.20 D when dw is equal to 0.03 mm,
1.09 D≦n≦2.40 D when dw is equal to 0.04 mm,
0.87 D≦n≦1.92 D when dw is equal to 0.05 mm,
0.73 D≦n≦1.60 D when dw is equal to 0.06 mm,
0.62 D≦n≦1.37 D when dw is equal to 0.07 mm,
0.55 D≦n≦1.20 D when dw is equal to 0.08 mm,
0.49 D≦n≦1.06 D when dw is equal to 0.09 mm,
0.44 D≦n≦0.96 D when dw is equal to 0.10 mm, and
0.37 D≦n≦0.80 D when dw is equal to 0.12 mm, wherein "dw" represents a diameter of a strand of each strand bundle in the plurality of strand bundles and "D" represents an average diameter of the netted tube.

In yet another aspect of the present invention, a netted tube, formed by braiding a plurality of strand bundles each formed by closely arranging a plurality of fine wires in parallel, is used in a flexible tube for an endoscope. The flexible tube has a spiral tube and a jacket. The netted tube covers an outer surface of the spiral tube. The jacket is made of a flexible synthetic resin which covers an outer surface of the netted tube. The following relationships are satisfied:

$$45° \leq \alpha \leq 65°,$$

$$0.772 \leq K \leq 0.906$$

and $$n = 16,$$

wherein "$\alpha$" represents a braid angle, "K" represents a braid density, and "n" represents a number of strands contained in one of the plurality of strand bundles. The number "n" satisfies the following relationships:

4.34 D≦n≦9.62 D when dw is equal to 0.02 mm,
2.89 D≦n≦6.41 D when dw is equal to 0.03 mm,
2.17 D≦n≦4.81 D when dw is equal to 0.04 mm,
1.74 D≦n≦3.84 D when dw is equal to 0.05 mm,
1.45 D≦n≦3.20 D when dw is equal to 0.06 mm,
1.24 D≦n≦2.74 D when dw is equal to 0.07 mm,
1.09 D≦n≦2.40 D when dw is equal to 0.08 mm,
0.97 D≦n≦2.13 D when dw is equal to 0.09 mm,
0.87 D≦n≦1.92 D when dw is equal to 0.10 mm, and
0.73 D≦n≦1.60 D when dw is equal to 0.12 mm, wherein "dw" represents a diameter of a strand of each strand bundle in the plurality of strand bundles and "D" represents an average diameter of the netted tube.

In another aspect of the present invention, a netted tube, formed by braiding a plurality of strand bundles each formed by closely arranging a plurality of fine wires in parallel, is used in a flexible tube for an endoscope. The flexible tube has a spiral tube and a jacket. The netted tube covers an outer surface of the spiral tube. The jacket is made of a flexible synthetic resin which covers an outer surface of the netted tube. The following relationships are satisfied:

$$45° \leq \alpha \leq 65°,$$

$$0.772 \leq K \leq 0.906$$

and $$n = 8,$$

wherein "$\alpha$" represents a braid angle, "K" represents a braid density, and "n" represents a number of strands contained in one of the plurality of strand bundles. The number "n" satisfies the following relationships:

8.67 D≦n≦19.24 D when dw is equal to 0.02 mm,
5.78 D≦n≦12.82 D when dw is equal to 0.03 mm,
4.34 D≦n≦9.62 D when dw is equal to 0.04 mm,
3.47 D≦n≦7.69 D when dw is equal to 0.05 mm,
2.89 D≦n≦6.41 D when dw is equal to 0.06 mm,
2.48 D≦n≦5.49 D when dw is equal to 0.07 mm, and
2.17 D≦n≦4.81 D when dw is equal to 0.08 mm, wherein "dw" represents a diameter of a strand of each strand bundle in the plurality of strand bundles and "D" represents an average diameter of the netted tube.

The present disclosure relates to subject matter contained in Japanese Patent Applications No. 7-206878 (filed on Aug. 14, 1995), No. 7-206879 (filed on Aug. 14, 1995), No. 7-215780 (filed on Aug. 24, 1995), No. 7-215781 (filed on Aug. 24, 1995), No. 7-215782 (filed on Aug. 24, 1995), No. 7-215783 (filed on Aug. 24, 1995) which are expressly incorporated herein by reference in their entireties.

BRIEF DESCRIPTION OF THE DRAWINGS

The present invention will be described below in detail with reference to the accompanying drawings, in which similar members are indicated by similar reference numerals, and wherein:

FIG. 4 is a table showing details regarding a first embodiment of a flexible tube for an endoscope;

FIG. 6 is a table showing details regarding a second embodiment of a flexible tube for an endoscope;

FIG. 7 is a table showing details regarding a third embodiment of a flexible tube for an endoscope;

FIG. 8 is a table showing details regarding a fourth embodiment of a flexible tube for an endoscope;

FIG. 9 is a table showing details regarding a fifth embodiment of a flexible tube for an endoscope;

FIG. 10 is a sectional view of a strand for a netted tube of the fifth embodiment;

FIG. 32 is a table showing details regarding a twenty-seventh embodiment of a flexible tube for an endoscope;

FIG. 33 is a table showing details regarding a twenty-eighth embodiment of a flexible tube for an endoscope;

FIG. 34 is a table showing details regarding a twenty-ninth embodiment of a flexible tube for an endoscope;

FIG. 35 is a table showing details regarding a thirtieth embodiment of a flexible tube for an endoscope;

DESCRIPTION OF THE PREFERRED EMBODIMENTS

Figure 2:
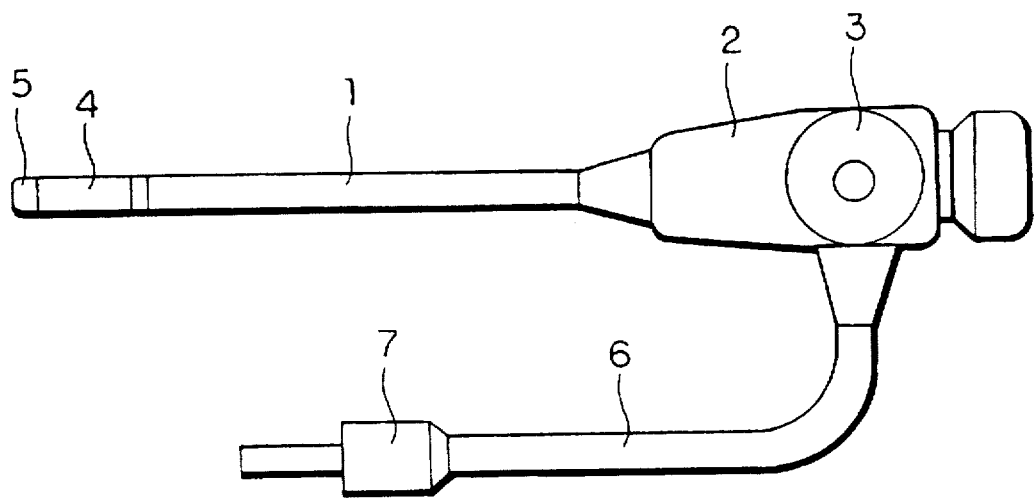
FIG. 2 is a side view of an endoscope provided with the flexible tube shown in FIG. 1.

FIG. 2 shows an endoscope having a bendable portion 4 formed at the end of a flexible tube 1. A curvature adjusting knob 3 is mounted on a manipulating section 2. The bendable portion 4 is remotely bent by rotating the curvature adjusting knob 3. A channel outlet (not shown) is provided inside the flexible tube 1, through which forceps etc. can be inserted. One end of the channel outlet is connected to the manipulating section 2.

A distal end portion 5 is connected to the outermost end of the bendable portion 4. An objective optical system (not shown) or the like is provided inside the distal end portion 5. A flexible connecting cord 6 is connected to the manipulating section 2. The flexible connecting cord 6 is provided at an end thereof with a connector 7 that can be connected to a light source device (not shown).

Figure 1:
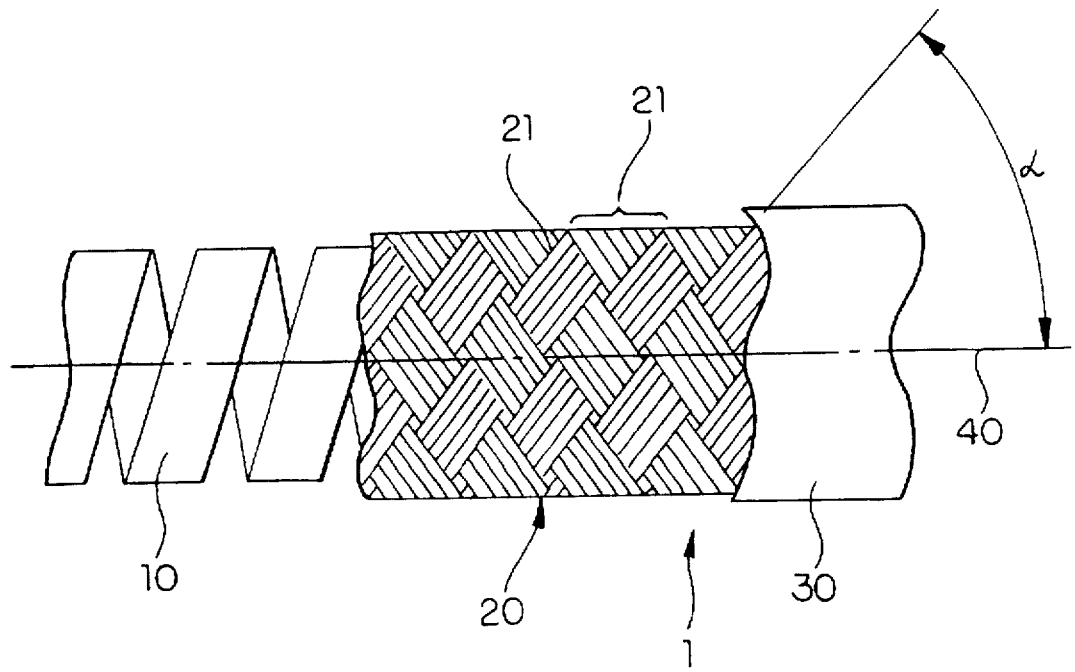
FIG. 1 is a partially cut-out side view of a flexible tube for an endoscope.

FIG. 1 shows an arrangement of the flexible tube 1. The flexible tube 1 is provided with a spiral tube 10. The spiral tube 10 is formed by spirally winding a metal belt of a stainless steel, a copper alloy or the like in a uniform diameter. The metal belt is wound by a single spiral or more than one spiral (e.g., double spirals).

Reference numeral 20 denotes a netted tube which covers the spiral tube 10. The netted tube 20 is formed by braiding a plurality of strand bundles 21. Each of the plurality of strand bundles 21 consists of a plurality of strands consisting of metal fine wires closely arranged in parallel. The metal fine wires may be made of a stainless steel, a copper alloy (e.g., phosphor bronze or a beryllium bronze), a tungsten steel, etc. In this specification, the number of strands contained in one strand bundle 21 is designated by "n", while the number of strand bundles 21 to be braided is designated as "m".

The netted tube 20 closely covers the spiral tube 10. Both ends of the netted tube 20 and the spiral tube 10 are fixed by soldering or the like. Due to this structure, the flexible tube 1 is prevented from being extended and twisted. An angle α defined between an axis 40 of the flexible tube 1 and each strand in the strand bundle 21 is called a braid angle.

Figure 37:
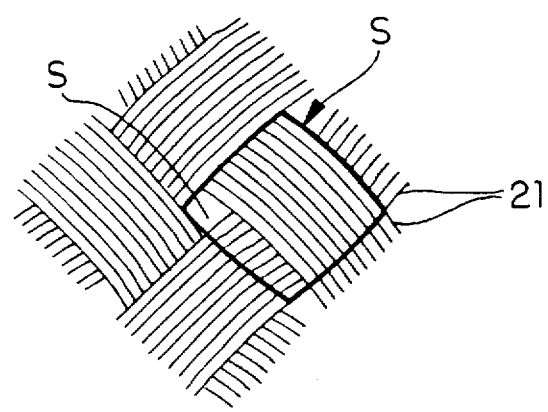
FIG. 37 is an illustration showing the braid density of a netted tube.

In the first through fifth embodiments, the braid density K of the netted tube 20 is arranged to be within an approximate range of $0.78 \leq K \leq 0.90$, specifically, within a range of $0.772 \leq K \leq 0.906$. As previously described, the braid density K is a ratio of the area of the strand bundle 21 covering the outer surface of the netted tube 20, namely $K=(S-s)/S$, as shown in FIG. 37 ($K=1$ if there is no gap between the strand bundles).

Reference numeral 30 designates a flexible jacket. The flexible jacket 30 covers an outer surface of the netted tube 20. The flexible jacket 30 is formed of synthetic resin, such as polyurethane. The flexible jacket 30 penetrates into the gaps in the netted tube 20 from outside.

After the spiral tube 10 has been covered with the netted tube 20, the outer surface of the netted tube 20 is covered by the flexible jacket 30 using one of the following two methods. In each of the first through fifth embodiments (described later), it was found that the flexible jackets prepared by both methods shared a similar bonding strength.

Figure 3:
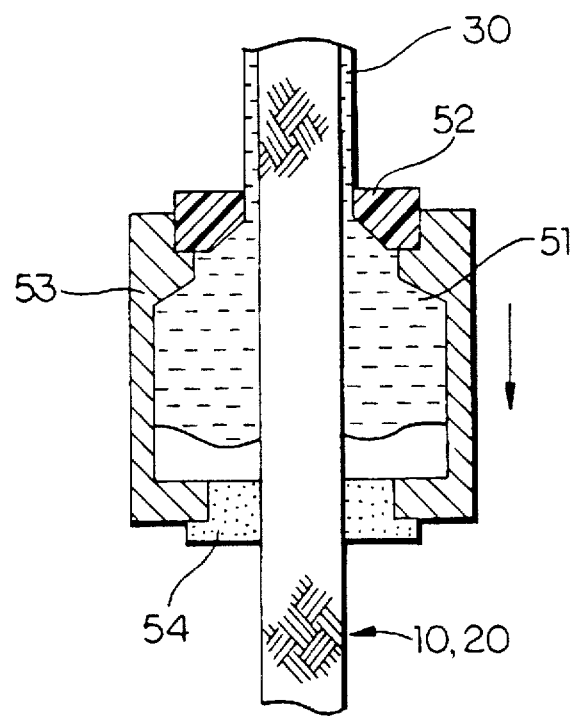
FIG. 3 is a front sectional view illustrating a method for covering the outer surface of the flexible tube for an endoscope.

FIG. 3 shows a first processing method for covering the netted tube 20 with the flexible jacket 30. In this method, a synthetic resin compound 51 is prepared by dissolving, for example, an amount of polyurethane elastomer pellet in a solvent having twice the amount, and is applied on the surface of the netted tube 20 through a die 52.

A compound container 53 is integrally provided on a bottom surface of the die 52. To form the flexible jacket 30 the following operation is performed, namely, while the compound 51 is applied to the netted tube 20, the die 52 is moved downward along the length of the netted tube 20 due to the weight of the compound container 53. The amount of the compound 51 applied to the netted tube 20 is defined by the thickness of the inner diameter of the die 52. Reference numeral 54 designates a sponge.

The above operation is performed three times, until the outer diameter of the flexible jacket 30 meets predetermined dimensions. The inner diameter of the die 52 is increased for each operation. After the formation of the outer diameter of the flexible jacket 30 is complete, the flexible jacket 30 is left for evaporation of the solvent so that the flexible jacket 30 is hardened.

Although not shown, a second processing method for covering the netted tube 20 with the flexible jacket 30 is known. In this method, the outer surface of the netted tube 20 is covered by a tube, formed of, for example, thermo-plastic polyurethane elastomer. Heat having a temperature higher than the softening point of the tube (for example, heating for 10 minutes at 200° C.) is then applied to the tube. After the molten tube has penetrated into the gaps formed between the strand bundles of the netted tube 20, the tube is left to cool.

The first through fifth embodiments will now be discussed with reference to tables shown in FIGS. 4, 6, 7, 8 and 9. In the following tables a lateral arrow designates that the value is the same as the value to the left.

Figure 5:
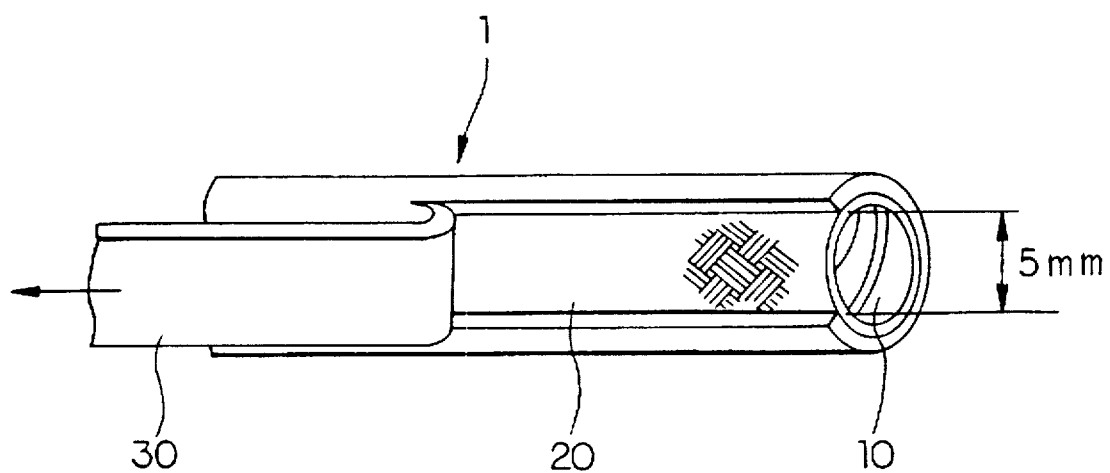
FIG. 5 is a side view illustrating a peel strength measuring method for the first embodiment.

In each of the first through fifth embodiments, several types of flexible tube 1 were evaluated. One of the tests used to evaluate the different types of flexible tube 1 included the peeling test. The peeling test is performed, as shown in FIG. 5, by cutting a 5 mm wide strip of the resultant jacket of the flexible tube 1 in the axial direction with a razor blade, pulling the slit section with a spring scale, and reading the scale when it is peeled.

[Embodiment 1]

FIG. 4 is a table showing details regarding the first embodiment. In the first embodiment, five types of flexible tube 1 (1)–(5) having different strand diameters and different numbers of strands in one bundle (n) of the netted tube 20 were prepared and evaluated for use as a flexible tube for an endoscope for the colon. The outer diameter of the five types of flexible tube 1 of the first embodiment was approximately 13 mm. The strands of the netted tube 20 were formed of stainless steel wires, each having a diameter of 0.1 mm.

In the case of type (1) of the present embodiment, having a braid density K of 0.715, while the flexible jacket 30 is highly permeable into the mesh of the netted tube 20, thus providing a good bonding property between the netted tube 20 and the flexible jacket 30, the flexible jacket 30 penetrates up until the spiral tube 10. This results in making bending difficult, and so the flexible tube 1 cannot be used for an endoscope.

In the cases of types (2) and (3) of the present embodiment, having a braid density K of 0.792 and 0.857, respectively, after cutting the flexible tube 1, a visual inspection of the inside of the flexible tube 1 revealed that the flexible jacket 30 penetrated into the netted tube 20, and that the bonding strength between the flexible jacket 30 and the netted tube 20 was sufficient to pass the peeling test.

In the case of type (4) of the present embodiment, having a braid density K of 0.91, while the flexible jacket 30 slightly penetrates into the netted tube 20, the amount of penetration was small so that the bonding strength between the netted tube 20 and the jacket 30 was poor.

In the case of type (5) of the present embodiment, having a braid density K of 0.951, since the flexible jacket 30 did not penetrate into the netted tube 20, but remained on the outer surface, the bonding strength was somewhat poor. Therefore, in the case of type (5), if the flexible tube 1 is bent by an amount having a small radius of curvature, the flexible jacket 30 can easily separate from the netted tube 20, thus causing creasing to occur.

[Embodiment 2]

FIG. 6 is a table showing details regarding the second embodiment. In the second embodiment, five types of flexible tube 1 (1)–(5) each having different strand diameters and different numbers of strands in one bundle (n) of the netted tube 20 were prepared and evaluated for use as a flexible tube for an endoscope for the upper alimentary canal. The outer diameter of the five types of flexible tube 1 of the second embodiment was approximately 9 mm. The strands of the netted tube 20 were formed of stainless steel wires, each having a diameter of 0.08 mm.

For this second embodiment and subsequent embodiments (i.e., third, fourth and fifth embodiments) having a flexible tube 1 having a relatively small outer diameter (compared with the first embodiment), since linear peeling conditions cannot be attained if the flexible jacket 30 is slit with a 5 mm interval, and since a part of the flexible jacket 30 is often torn off if the flexible jacket 30 is slit and stretched by less than a 5 mm interval, the peeling strength cannot be measured. Thus, in embodiments 2 through 5, bonding between the netted tube 20 and the flexible jacket 30 is determined from the penetration of the netted tube 20 into the flexible jacket 30.

The results obtained from the present embodiment showed that type (1) having a braid density K of 0.711 and type (5) having a braid density K of 0.948 were not acceptable, while type (2) having a braid density K of 0.788, type (3) having a braid density K of 0.853, and type (4) having a braid density K of 0.906, were acceptable.

[Embodiment 3]

FIG. 7 is a table showing details regarding the third embodiment. In the third embodiment, five types of flexible tube 1 (1)–(5) having different strand diameters and different numbers of strands in one bundle (n) of the netted tube 20 were prepared and evaluated for use as a flexible tube for an endoscope for the bronchus. The outer diameter of the five types of flexible tube 1 of the third embodiment was approximately 5 mm. The strands of the netted tube 20 were formed of stainless steel wires, each having a diameter of 0.05 mm.

The results obtained from the present embodiment showed that type (1) having a braid density K of 0.705 and type (5) having a braid density K of 0.92 were not acceptable, while type (2) having a braid density K of 0.772, type (3) having a braid density K of 0.83, and type (4) having a braid density K of 0.879 were acceptable.

[Embodiment 4]

FIG. 8 is a table showing details regarding the fourth embodiment. In the fourth embodiment, six types of flexible tube 1 (1)–(6) having different strand diameters and different numbers of strands in one bundle (n) of the netted tube 20 were prepared and evaluated for use as a flexible tube for an endoscope for the bronchus or otolaryngology. The outer diameter of the six types of flexible tube 1 was approximately 3.5 mm. The strands of the netted tube 20 were formed of stainless steel wires, each having a diameter of 0.03 mm.

The results obtained from the present embodiment showed that type (1) having a braid density K of 0.735, type (5) having a braid density K of 0.911, and type (6) having a braid density K of 0.94 were not acceptable, while type (2) having a braid density K of 0.788, type (3) having a braid density K of 0.835, and type (4) having a braid density K of 0.876 were acceptable.

[Embodiment 5]

FIG. 9 is a table showing details regarding the fifth embodiment. In the fifth embodiment, four types of flexible tube 1 (1)–(4) having different strand diameters and different numbers of strands in one bundle (n) of the netted tube 20 were prepared and evaluated for use as a flexible tube for an endoscope for the bronchus. The outer diameter of the four types of flexible tube 1 was approximately 4.2 mm.

In this embodiment, the netted tube 20 was braided with strands having a flat section of 0.022 mm thickness and a width of 0.089 mm, as shown in FIG. 10. Each of the strands was formed by crushing a fine wire having a diameter of 0.05 mm.

Type (1) having a braid density K of 0.659 and type (4) having a braid density K of 0.972 were not acceptable, while type (2) having a braid density K of 0.801, and type (3) having a braid density K of 0.906 were acceptable.

Each of the above first through fifth embodiments was tested using strands formed of copper alloy wires for the netted tube 20. The results obtained showed no significant difference from the results of the embodiments using strands formed of stainless steel.

According to any one of the above first through fifth embodiments, since high bonding strength can be obtained between the netted tube and the flexible jacket when the braid density K is arranged to be less than or equal to 0.906 ($K \leq 0.906$), creases hardly occur, even if the flexible tube is bent by an amount having a small radius of curvature. In addition, since the braid density K is arranged to be greater than or equal to 0.772 ($0.772 \leq K$), the flexible jacket does not bind to the spiral tube, and thus the flexible tube can be smoothly bent and has a good insertion capability for insertion into a body cavity.

Sixth through ninth embodiments will be hereinafter discussed with reference to FIGS. 11 through 14. The overall structure of the endoscope in each of the sixth through ninth embodiments is identical to that shown in FIG. 2. In each of the sixth through ninth embodiments, similar to each of the first through fifth embodiments, each of the plurality of strand bundles 21 consists of a plurality of strands consisting of metal fine wires closely arranged in parallel. The metal fine wires may be made of a stainless steel, a copper alloy (e.g., phosphor bronze or a beryllium bronze), a tungsten steel, etc. In addition, in the sixth through ninth embodiments, the number of strand bundles to be braided "m" is fixed to be 24 (m=24).

In order to prevent the flexible tube 1 from buckling when it is repeatedly bent by an amount having a small radius of curvature, Japanese Laid-Open Patent Application No. 62-133925 has disclosed an appropriate method in which the above-noted angle α of the netted tube 20 should be set within a range of 45 degrees to 65 degrees ($45° \leq \alpha \leq 65°$).

The braid density K of the netted tube 20 can be expressed by the following relationships:

$$K = 2F - F^2 \qquad \text{①}$$

$$F = m \times n \times dw / (2P \times \sin \alpha) \qquad \text{②},$$

wherein

"F" represents a filling factor,

"m" represents the number of strand bundles 21 to be braided,

"n" represents the number of strands contained in one strand bundle 21,

"dw" represents the diameter of a strand in each strand bundle 21 [mm], and

"P" represents the braid pitch [mm].

Since $$P = \pi \times D / \tan \alpha \qquad \text{③},$$

according to the above relationships ① and ②, the following relationship is obtained:

$$n = (2\pi \times \sin \alpha \times F) \times D / dw \times m \times \tan \alpha \qquad \text{④},$$

wherein "D" represents the average diameter of the netted tube 20 (i.e., the outer diameter of the spiral tube 10 plus 2 dw [mm]).

By incorporating the aforementioned condition "$0.772 \leq K \leq 0.906$" obtained in the first through fifth embodiments, the value of "F" obtained according to the above relationship ①, and the aforementioned condition "45°≦α≦65°" into the above relationship ④, the number "n" of strands contained in one strand bundle 21 with respect to the average diameter of the netted tube 20 can be determined as follows:

2.89 D≦n≦6.41 D when dw is equal to 0.02 mm,
1.93 D≦n≦4.27 D when dw is equal to 0.03 mm,
1.45 D≦n≦3.20 D when dw is equal to 0.04 mm,
1.16 D≦n≦2.56 D when dw is equal to 0.05 mm,
0.97 D≦n≦2.13 D when dw is equal to 0.06 mm,
0.83 D≦n≦1.83 D when dw is equal to 0.07 mm,
0.73 D≦n≦1.60 D when dw is equal to 0.08 mm,
0.65 D≦n≦1.42 D when dw is equal to 0.09 mm,
0.58 D≦n≦1.28 D when dw is equal to 0.10 mm, and
0.49 D≦n≦1.06 D when dw is equal to 0.12 mm, wherein "n" is an integral number because of its nature.

If the number "n" is large, it becomes difficult and thus time consuming to braid the netted tube 20. Therefore, it is preferable that the number "n" should be less than thirteen (i.e., 1≦n≦12). Due to this reason, it is preferable that the maximum value of the average diameter "D" of the netted tube 20 with respect to the diameter "dw" of a strand in each strand bundle 21 should satisfy the following conditions:

1.9 mm≦D≦4.1 mm when dw is equal to 0.02 mm,
2.9 mm≦D≦6.2 mm when dw is equal to 0.03 mm,
3.8 mm≦D≦8.2 mm when dw is equal to 0.04 mm,
4.7 mm≦D≦10.3 mm when dw is equal to 0.05 mm,
5.7 mm≦D≦12.3 mm when dw is equal to 0.06 mm,
6.6 mm≦D≦14.4 mm when dw is equal to 0.07 mm,
7.5 mm≦D≦16.4 mm when dw is equal to 0.08 mm,
8.5 mm≦D≦18.4 mm when dw is equal to 0.09 mm,
9.4 mm≦D≦20.6 mm when dw is equal to 0.10 mm, and
11.4 mm≦D≦24.4 mm when dw is equal to 0.12 mm.

[Embodiment 6]

Figure 11:
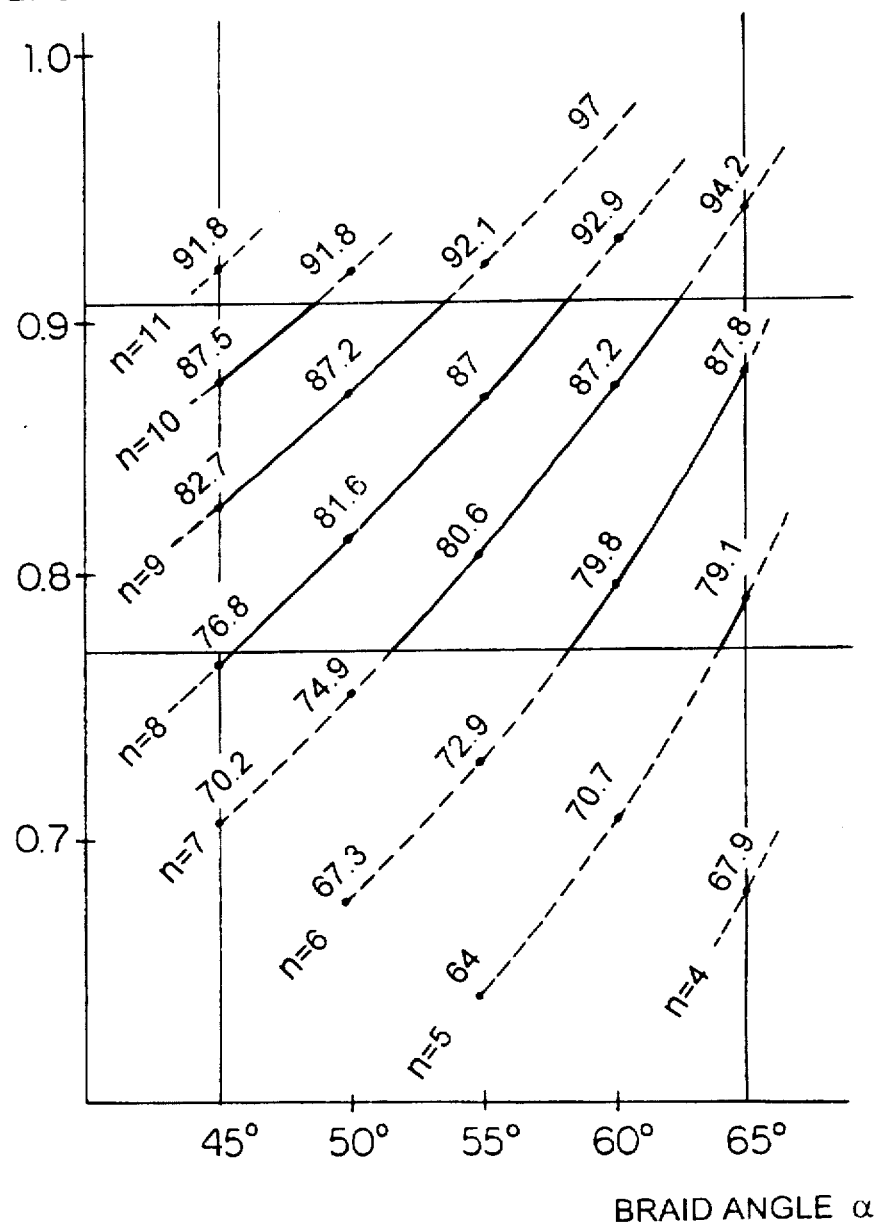
FIG. 11 is a graph showing the relationships among a braid density, a braid angle α and the number n of strands contained in one strand bundle in a sixth embodiment of a flexible tube for an endoscope.

FIG. 11 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 10 mm, 24 and 0.12 mm, respectively. As can be understood from the graph shown in FIG. 11, the number "n" which satisfies both the aforementioned conditions "45°≦α≦65°" and "0.772≦K≦0.906" must lie in a range of "5≦n≦10". It should be noted that the numerical numbers written along the lines in each graph represent a percentage representing the braid density K.

[Embodiment 7]

Figure 12:
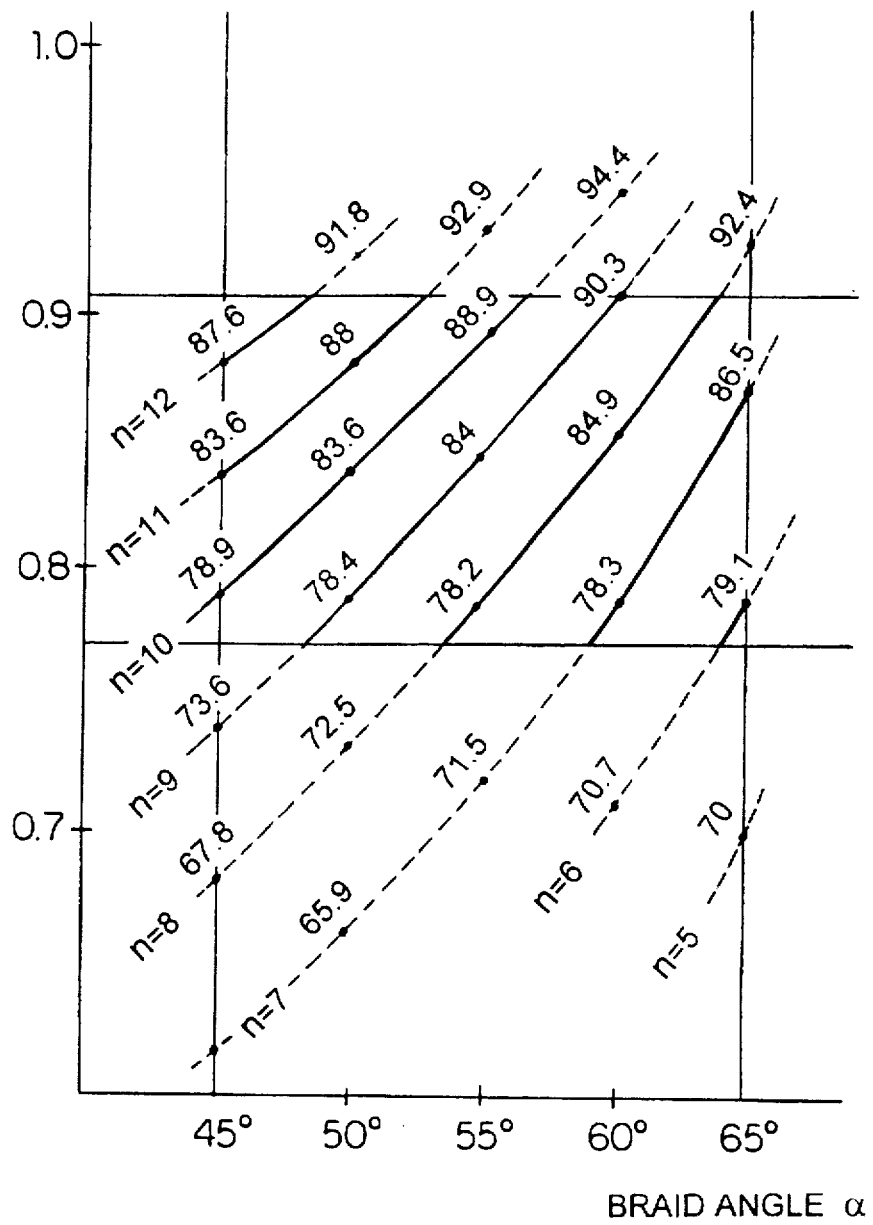
FIG. 12 is a graph showing the relationships among a braid density, a braid angle α and the number n of strands contained in one strand bundle in a seventh embodiment of a flexible tube for an endoscope.

FIG. 12 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 8 mm, 24 and 0.08 mm, respectively. As can be understood from the graph shown in FIG. 12, the number "n" which satisfies both the aforementioned conditions "45°≦α≦65°" and "0.772≦K≦0.906" must lie in a range of "6≦n≦12".

[Embodiment 8]

Figure 13:
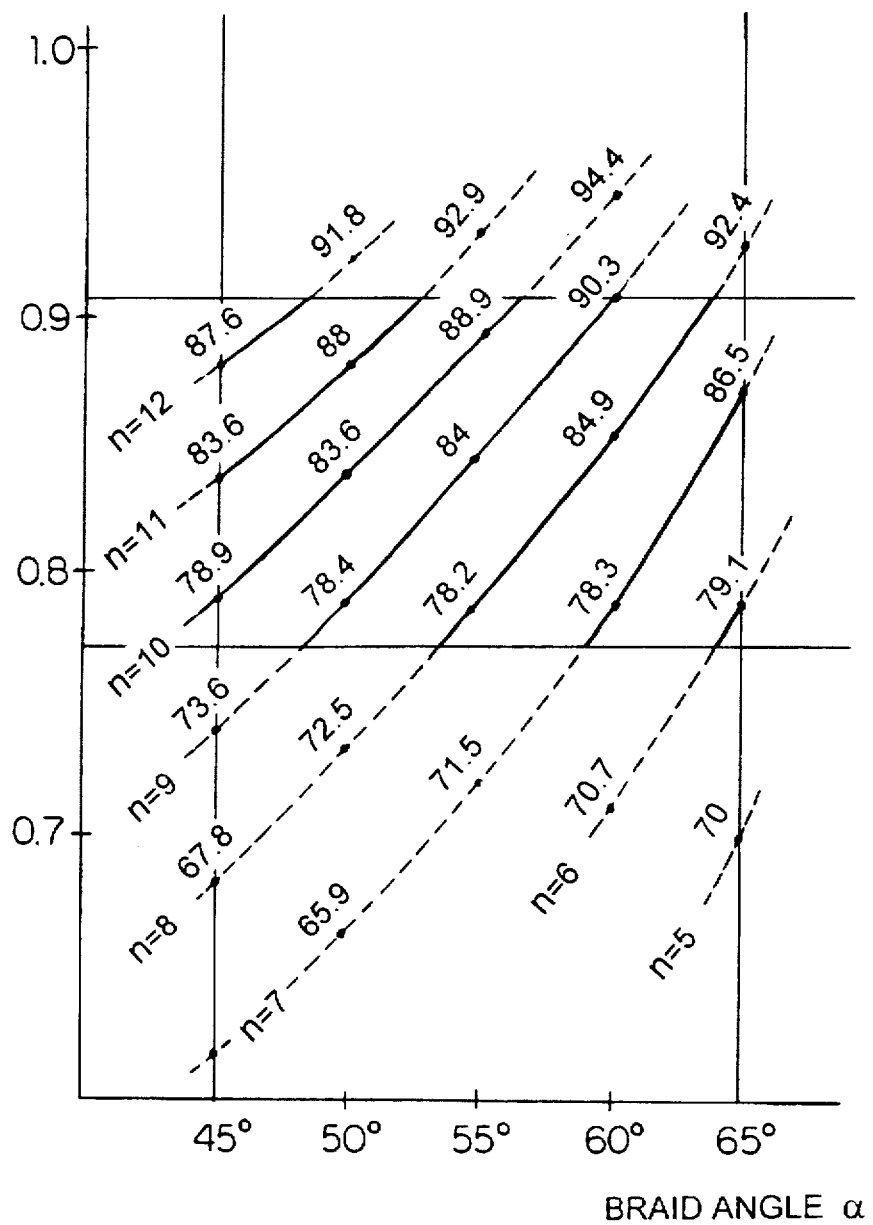
FIG. 13 is a graph showing the relationships among a braid density, a braid angle α and the number n of strands contained in one strand bundle in an eighth embodiment of a flexible tube for an endoscope.

FIG. 13 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 4 mm, 24 and 0.04 mm, respectively. As can be understood from the graph shown in FIG. 13, the number "n" which satisfies both the aforementioned conditions "45°≦α≦65°" and "0.772≦K≦0.906" must lie in a range of "6≦n≦12".

[Embodiment 9]

Figure 14:
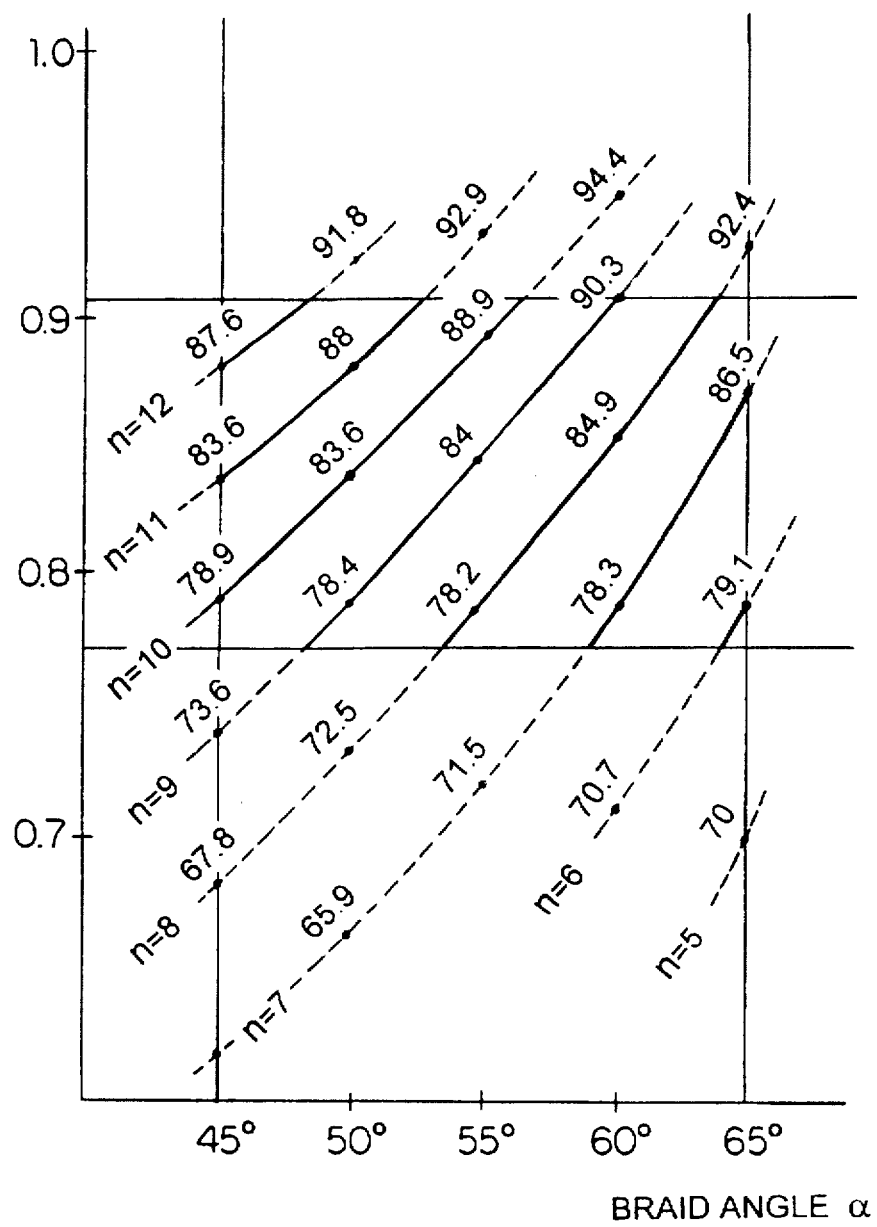
FIG. 14 is a graph showing the relationships among a braid density, a braid angle α and the number n of strands contained in one strand bundle in a ninth embodiment of a flexible tube for an endoscope.

FIG. 14 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 2 mm, 24 and 0.02 mm, respectively. As can be understood from the graph shown in FIG. 14, the number "n" which satisfies both the aforementioned conditions "45°≦α≦65°" and "0.772≦K≦0.906" must lie in a range of "6≦n≦12".

As can be understood from the foregoing, according to any one of the above sixth through ninth embodiments, in the netted tube having twenty four strand bundles to be braided, since the number of strands contained in one strand bundle with respect to the average diameter of the netted tube is determined within a predetermined range, both the aforementioned conditions "45°≦α≦65°" and "0.772≦K≦0.906" can be satisfied. Thus, once a netted tube, made according to any one of the above sixth through ninth embodiments, is combined with the flexible tube of an endoscope, a high bonding strength between the netted tube and the flexible jacket can be attained and the flexible tube can be smoothly bent. Therefore, the durability of the flexible tube greatly increases.

Tenth through fifteenth embodiments will be hereinafter discussed with reference to FIGS. 15 through 20. The tenth through fifteenth embodiments are similar to the sixth through ninth embodiments except that the number of strand bundles to be braided "m" is fixed to be 32 (m=32).

Therefore, by incorporating the aforementioned condition "0.772≦K≦0.906" obtained in the first through fifth embodiments, the value of "F" obtained according to the above relationship ①, and the aforementioned condition "45°≦α≦65°" into the above relationship ④, the number "n" of strands contained in one strand bundle 21 with respect to the average diameter of the netted tube 20 of the flexible tube 1 in the tenth through fifteenth embodiments can be determined as follows:

2.17 D≦n≦4.81 D when dw is equal to 0.02 mm,
1.45 D≦n≦3.20 D when dw is equal to 0.03 mm,
1.09 D≦n≦2.40 D when dw is equal to 0.04 mm,
0.87 D≦n≦1.92 D when dw is equal to 0.05 mm,
0.73 D≦n≦1.60 D when dw is equal to 0.06 mm,
0.62 D≦n≦1.37 D when dw is equal to 0.07 mm,
0.55 D≦n≦1.20 D when dw is equal to 0.08 mm,
0.49 D≦n≦1.06 D when dw is equal to 0.09 mm,
0.44 D≦n≦0.96 D when dw is equal to 0.10 mm, and
0.37 D≦n≦0.80 D when dw is equal to 0.12 mm, wherein "n" is an integral number because of its nature.

As mentioned above, it is preferable that the number "n" should be less than thirteen (i.e., 1≦n≦12). Due to this reason, it is preferable that the maximum value of the average diameter "D" of the netted tube 20 of the flexible tube 1 in the tenth through fifteenth embodiments with respect to the diameter "dw" of a strand in each strand bundle 21 should satisfy the following conditions:

2.5 mm≦D≦5.5 mm when dw is equal to 0.02 mm,
3.8 mm≦D≦8.2 mm when dw is equal to 0.03 mm,
5.0 mm≦D≦11.0 mm when dw is equal to 0.04 mm,
6.3 mm≦D≦13.7 mm when dw is equal to 0.05 mm,
7.5 mm≦D≦16.4 mm when dw is equal to 0.06 mm,
8.8 mm≦D≦19.3 mm when dw is equal to 0.07 mm,
10.0 mm≦D≦21.8 mm when dw is equal to 0.08 mm,
11.4 mm≦D≦24.4 mm when dw is equal to 0.09 mm,
12.5 mm≦D≦27.2 mm when dw is equal to 0.10 mm, and
15.0 mm≦D≦32.4 mm when dw is equal to 0.12 mm.

[Embodiment 10]

Figure 15:
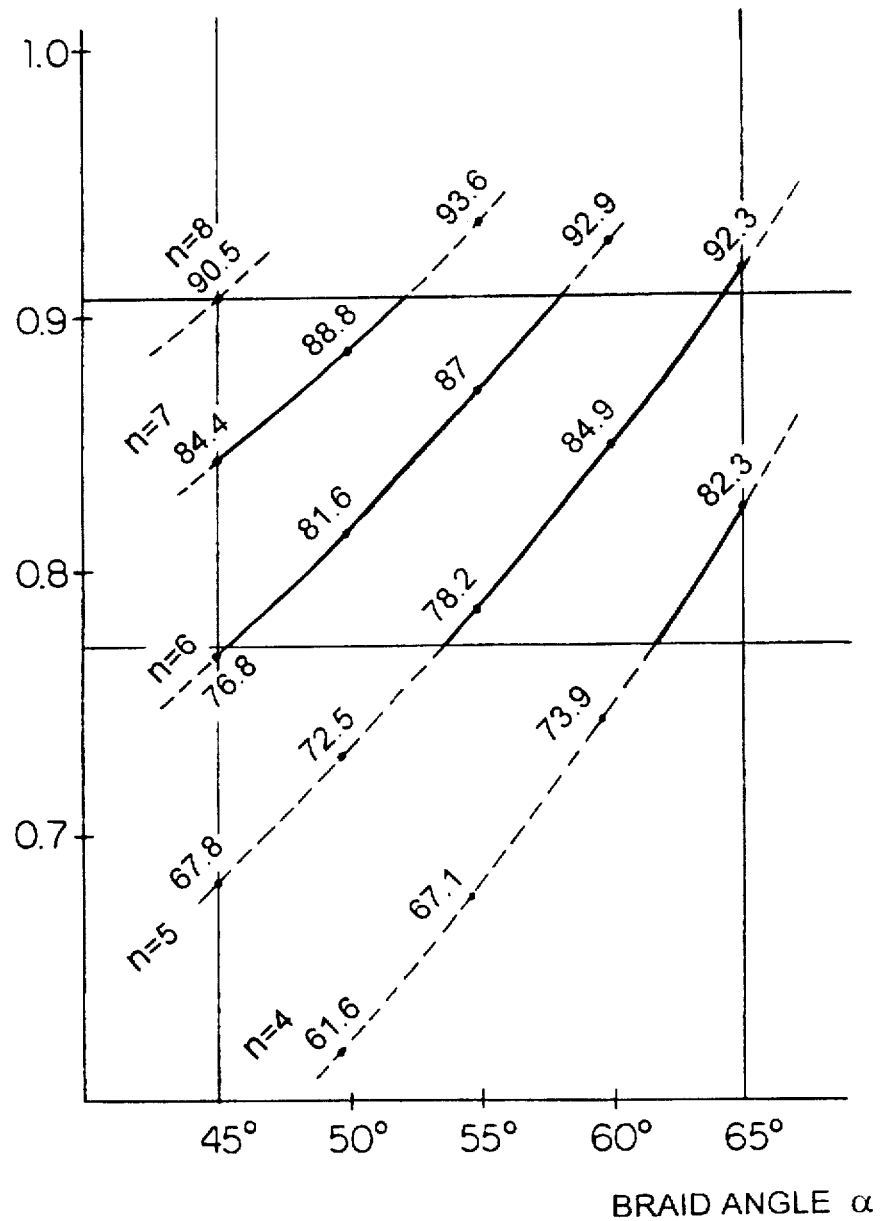
FIG. 15 is a graph showing the relationships among a braid density, a braid angle α and the number n of strands contained in one strand bundle in a tenth embodiment of a flexible tube for an endoscope.

FIG. 15 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 10 mm, 32 and 0.12 mm, respectively. As can be understood from the graph shown in FIG. 15, the number "n" which satisfies both the aforementioned conditions "45°≦α≦65°" and "0.772≦K≦0.906" must lie in a range of "4≦n≦8".

[Embodiment 11]

Figure 16:
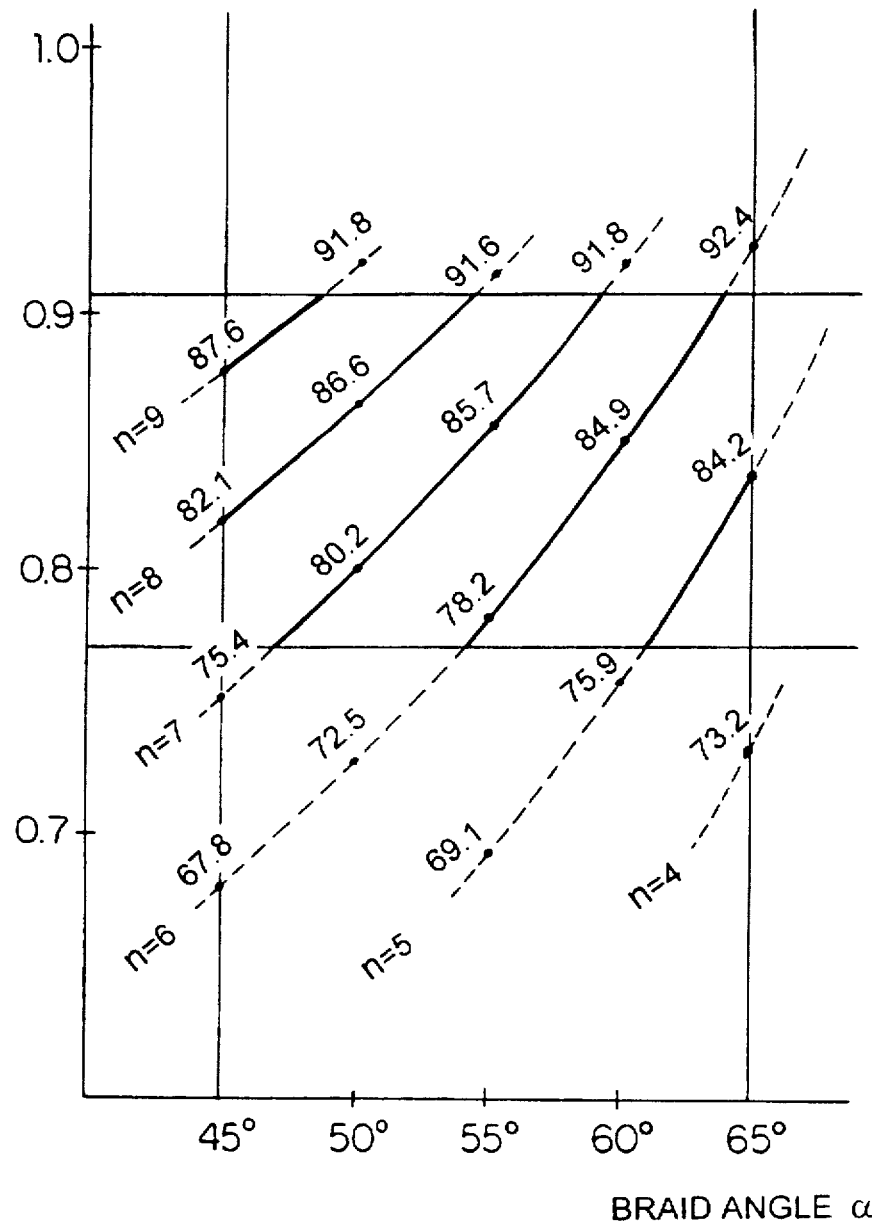
FIG. 16 is a graph showing the relationships among a braid density, a braid angle α and the number n of strands contained in one strand bundle in an eleventh embodiment of a flexible tube for an endoscope.

FIG. 16 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 8 mm, 32 and 0.08 mm, respectively. As can be understood from the graph shown in FIG. 16, the number "n" which satisfies both the aforementioned conditions "45°≦α≦65°" and "0.772≦K≦0.906" must lie in a range of "5≦n≦9".

[Embodiment 12]

Figure 17:
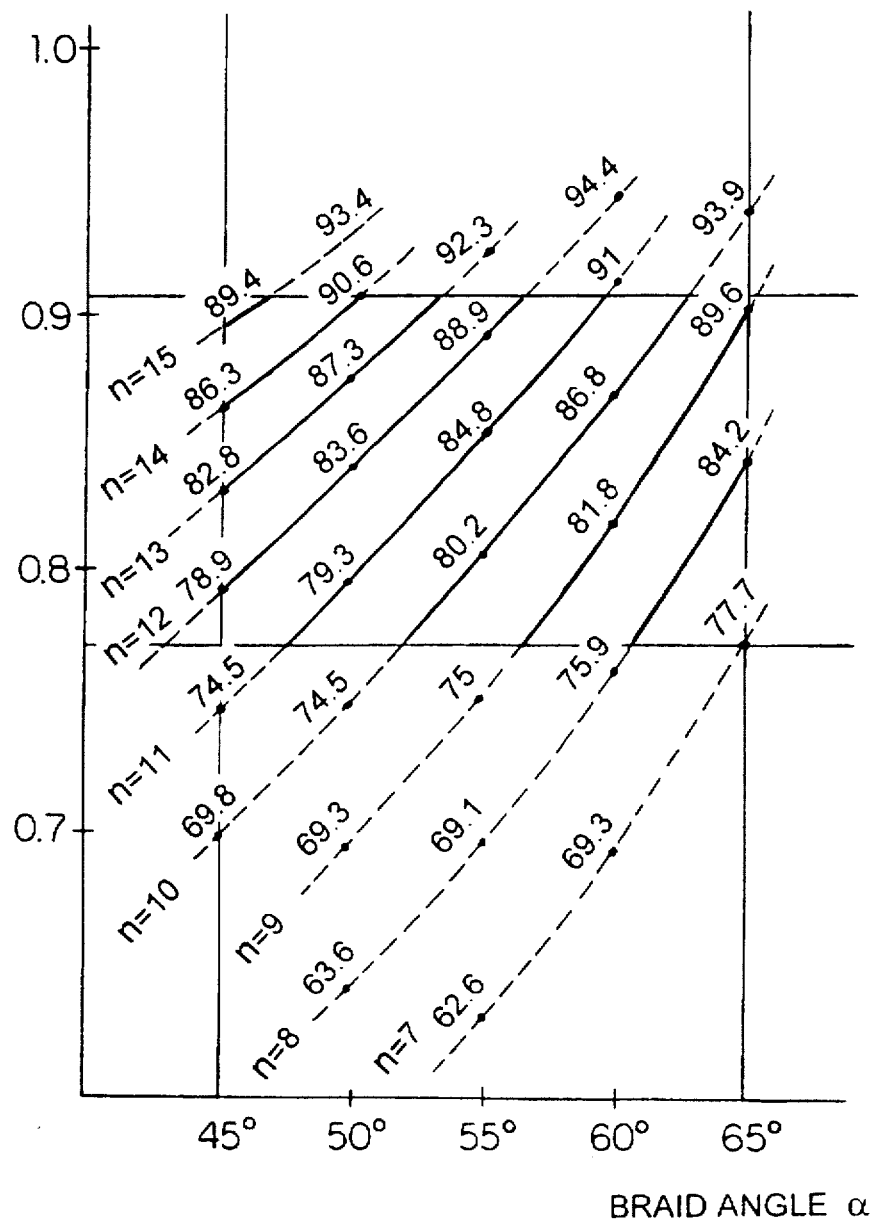
FIG. 17 is a graph showing the relationships among a braid density, a braid angle α and the number n of strands contained in one strand bundle in a twelfth embodiment of a flexible tube for an endoscope.

FIG. 17 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 6.4 mm, 32 and 0.04 mm, respectively. As can be understood from the graph shown in FIG. 17, the number "n" which satisfies both the aforementioned conditions "45°≦α≦65°" and "0.772≦K≦0.906" must lie in a range of "7≦n≦15".

[Embodiment 13]

Figure 18:
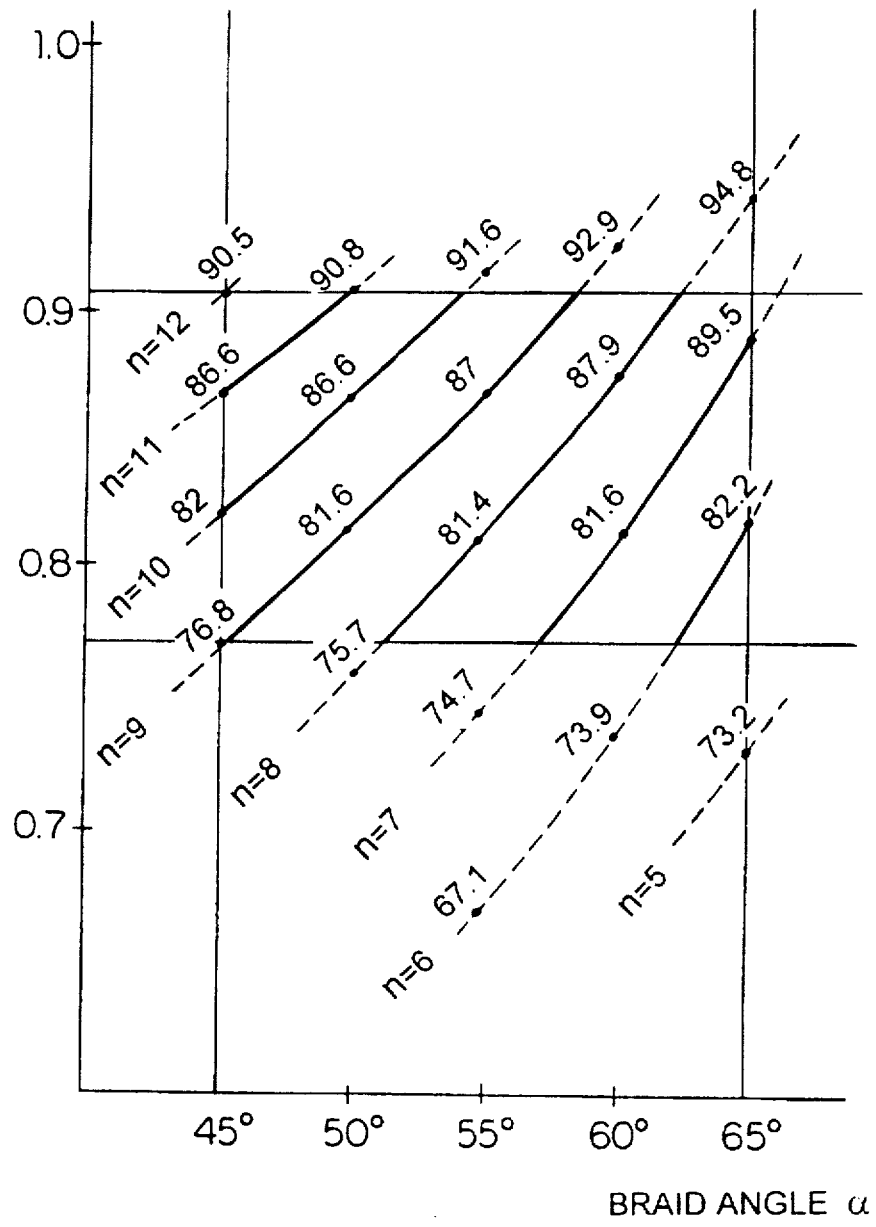
FIG. 18 is a graph showing the relationships among a braid density, a braid angle α and the number n of strands contained in one strand bundle in a thirteenth embodiment of a flexible tube for an endoscope.

FIG. 18 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 5 mm, 32 and 0.04 mm, respectively. As can be understood from the graph shown in FIG. 18, the number "n" which satisfies both the aforementioned conditions "45°≦α≦65°" and "0.772≦K≦0.906" must lie in a range of "6≦n≦12".

[Embodiment 14]

Figure 19:
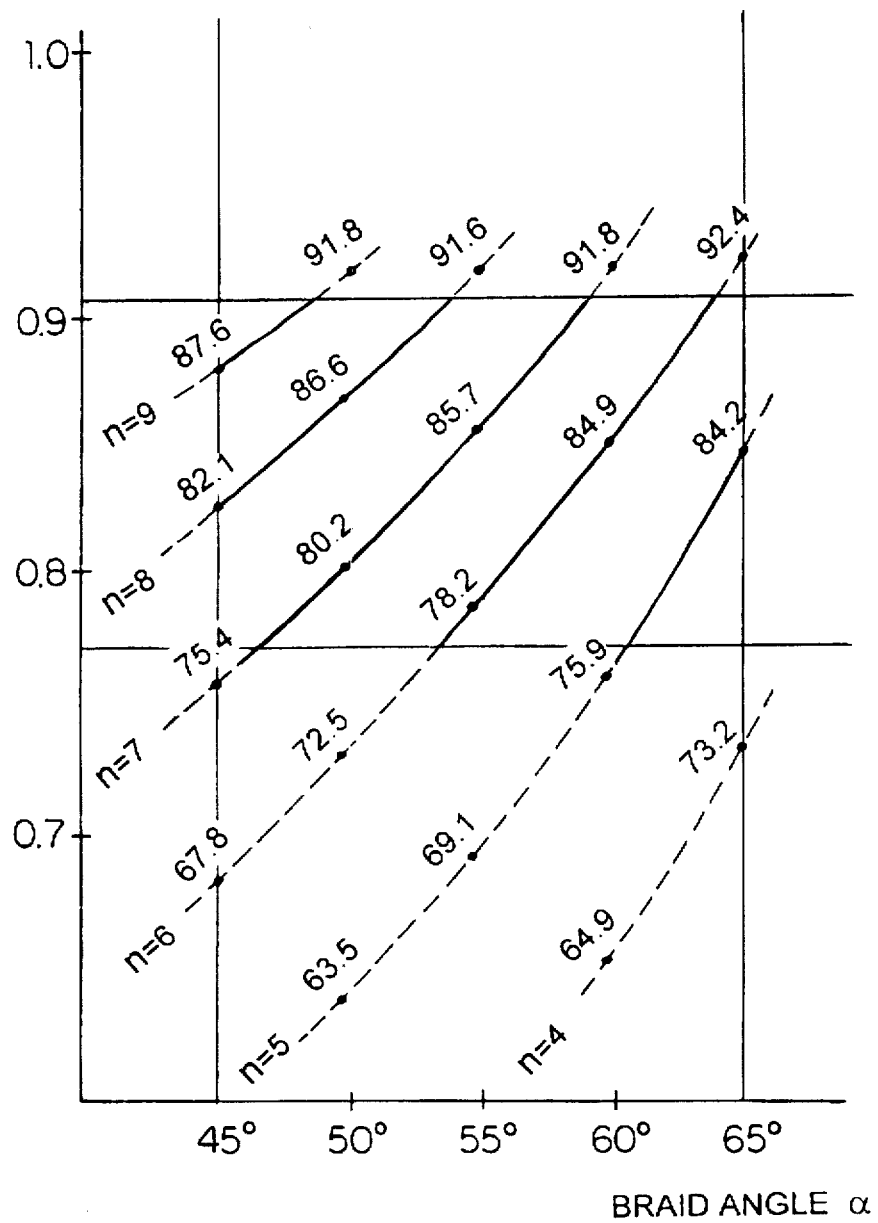
FIG. 19 is a graph showing the relationships among a braid density, a braid angle α and the number n of strands contained in one strand bundle in a fourteenth embodiment of a flexible tube for an endoscope.

FIG. 19 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 3 mm, 32 and 0.03 mm, respectively. As can be understood from the graph shown in FIG. 19, the number "n" which satisfies both the aforementioned conditions "45°≦α≦65°" and "0.772≦K≦0.906" must lie in a range of "5≦n≦9".

[Embodiment 15]

Figure 20:
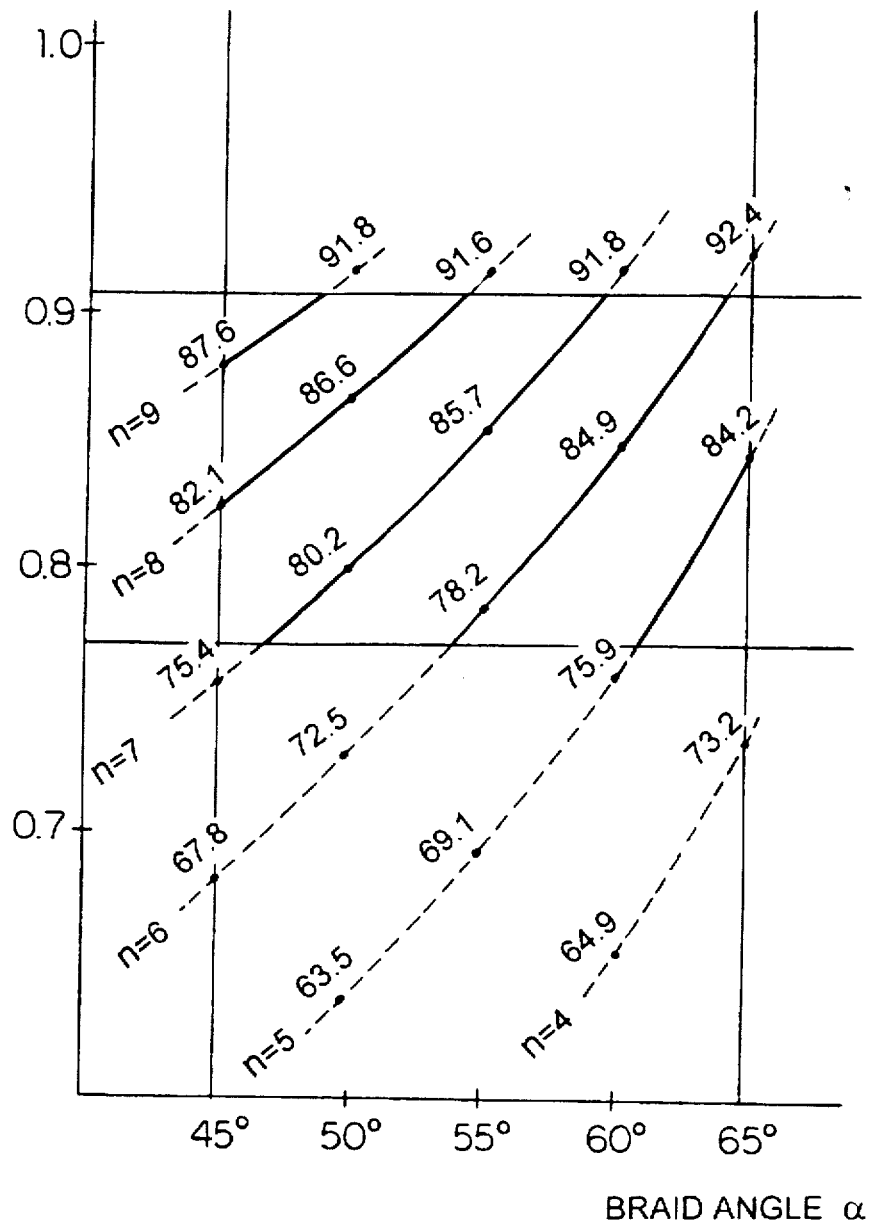
FIG. 20 is a graph showing the relationships among a braid density, a braid angle α and the number n of strands contained in one strand bundle in a fifteenth embodiment of a flexible tube for an endoscope.

FIG. 20 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 2 mm, 32 and 0.02 mm, respectively. As can be understood from the graph shown in FIG. 20, the number "n" which satisfies both the aforementioned conditions "45°≦α≦65°" and "0.772≦K≦0.906" must lie in a range of "5≦n≦9".

As can be understood from the foregoing, according to any one of the tenth through fifteenth embodiments, in the netted tube having thirty two strand bundles to be braided, since the number of strands contained in one strand bundle with respect to the average diameter of the netted tube is determined within a predetermined range, both the aforementioned conditions "45°≦α≦65°" and "0.772≦K≦0.906" can be satisfied. Thus, once a netted tube, made according to any one of the tenth through fifteenth embodiments, is combined with the flexible tube of an endoscope, a high bonding strength between the netted tube and the flexible jacket can be attained and the flexible tube can be smoothly bent. Therefore, the durability of the flexible tube greatly increases.

Sixteenth through twenty-second embodiments will be hereinafter discussed with reference to FIGS. 21 through 27. The sixteenth through twenty-second embodiments are similar to the sixth through ninth embodiments except that the number of strand bundles to be braided "m" is fixed to be 16 (m=16).

Therefore, by incorporating the aforementioned condition "0.772≦K≦0.906" obtained in the first through fifth embodiments, the value of "F" obtained according to the above relationship ①, and the aforementioned condition "45°≦α≦65°" into the above relationship ④, the number "n" of strands contained in one strand bundle 21 with respect to the average diameter of the netted tube 20 of the flexible tube 1 in the sixteenth through twenty-second embodiments can be determined as follows:

4.34 D≦n≦9.62 D when dw is equal to 0.02 mm,
2.89 D≦n≦6.41 D when dw is equal to 0.03 mm,
2.17 D≦n≦4.81 D when dw is equal to 0.04 mm,
1.74 D≦n≦3.84 D when dw is equal to 0.05 mm,
1.45 D≦n≦3.20 D when dw is equal to 0.06 mm,
1.24 D≦n≦2.74 D when dw is equal to 0.07 mm,
1.09 D≦n≦2.40 D when dw is equal to 0.08 mm,
0.97 D≦n≦2.13 D when dw is equal to 0.09 mm,
0.87 D≦n≦1.92 D when dw is equal to 0.10 mm, and
0.73 D≦n≦1.60 D when dw is equal to 0.12 mm, wherein "n" is an integral number because of its nature.

As above-mentioned, it is preferable that the number "n" should be less than thirteen (i.e., 1≦n≦12). Due to this reason, it is preferable that the maximum value of the average diameter "D" of the netted tube 20 of the flexible tube 1 in the sixteenth through twenty-second embodiments with respect to the diameter "dw" of a strand in each strand bundle 21 should satisfy the following conditions:

1.25 mm≦D≦2.76 mm when dw is equal to 0.02 mm,
1.88 mm≦D≦4.15 mm when dw is equal to 0.03 mm, 2.5 mm≦D≦5.5 mm when dw is equal to 0.04 mm,
3.2 mm≦D≦6.8 mm when dw is equal to 0.05 mm,
3.8 mm≦D≦8.2 mm when dw is equal to 0.06 mm,
4.4 mm≦D≦9.6 mm when dw is equal to 0.07 mm,
5 mm≦D≦11 mm when dw is equal to 0.08 mm,
5.7 mm≦D≦2.3 mm when dw is equal to 0.09 mm,
6.3 mm≦D≦13.7 mm when dw is equal to 0.10 mm, and
7.5 mm≦D≦16.4 mm when dw is equal to 0.12 mm.

[Embodiment 16]

Figure 21:
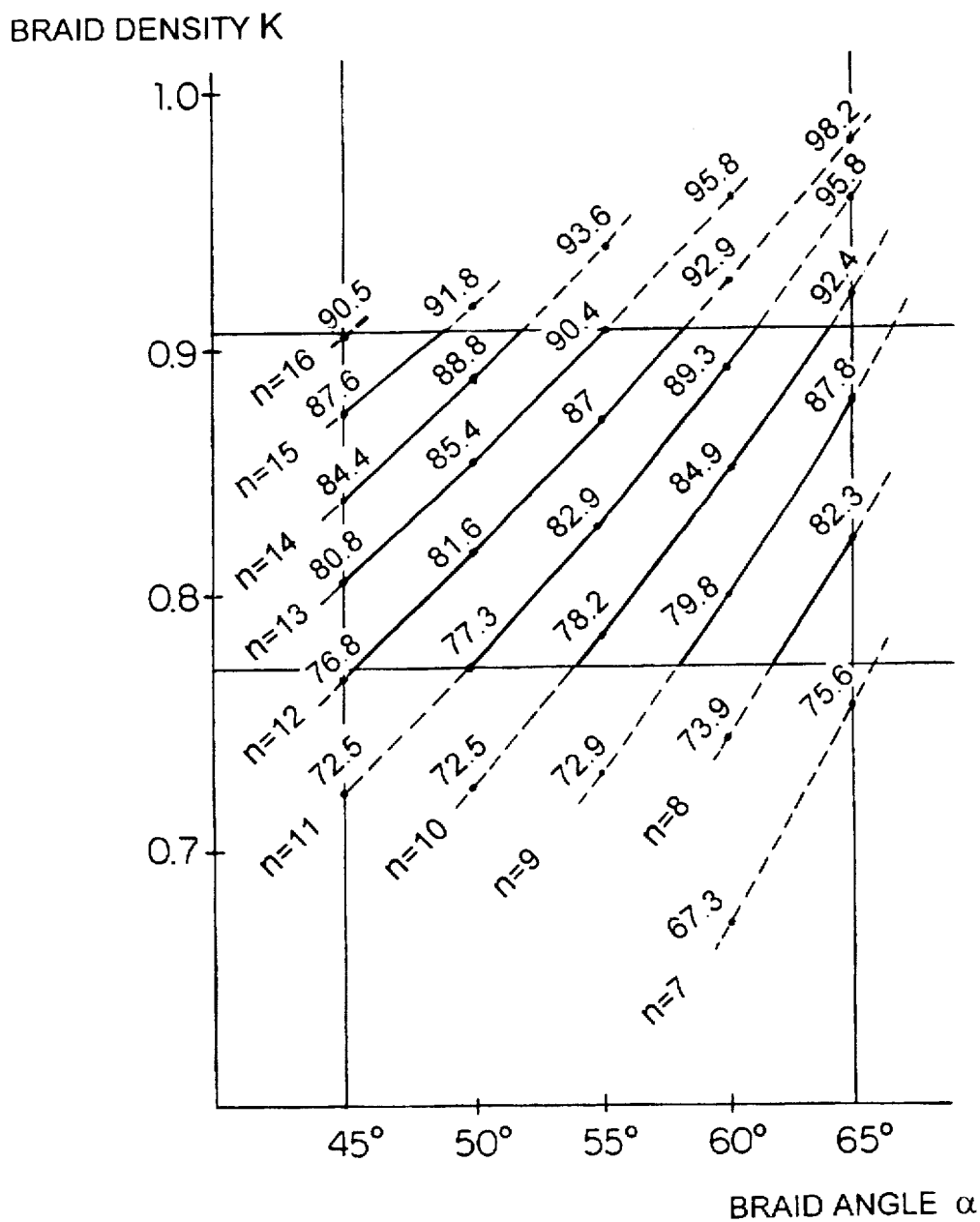
FIG. 21 is a graph showing the relationships among a braid density, a braid angle α and the number n of strands contained in one strand bundle in a sixteenth embodiment of a flexible tube for an endoscope.

FIG. 21 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 10 mm, 16 and 0.12 mm, respectively. As can be understood from the graph shown in FIG. 21, the number "n" which satisfies both the aforementioned conditions "45°≦α≦65°" and "0.772≦K≦0.906" must lie in a range of "8≦n≦16".

[Embodiment 17]

Figure 22:
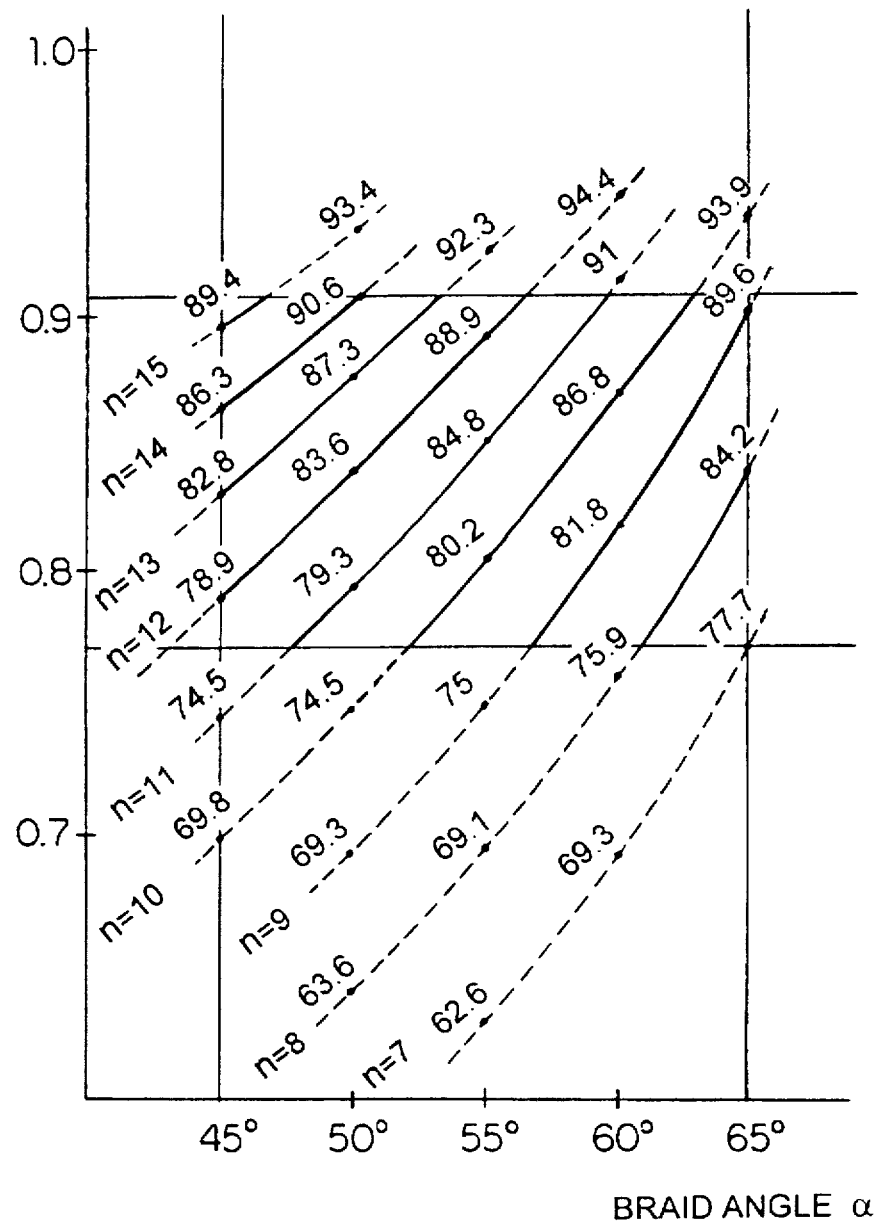
FIG. 22 is a graph showing the relationships among a braid density, a braid angle α and the number n of strands contained in one strand bundle in a seventeenth embodiment of a flexible tube for an endoscope.

FIG. 22 shows a graph showing the relationships among the braid density K (vertical axis), the braid angle α (horizontal axis) and the number n of strands contained in one strand bundle 21 under the condition that the average diameter of the netted tube "D", the number of strand bundles to be braided Amp and the diameter of a strand in each strand bundle "dw" are 8 mm, 16 and 0.1 mm, respectively. As can be understood from the graph shown in FIG. 22, the number "n" which satisfies both the aforementioned conditions "45°≦α≦65°" and "0.772≦K≦0.906" must lie in a range of "7≦n≦14".

[Embodiment 18]

Figure 23:
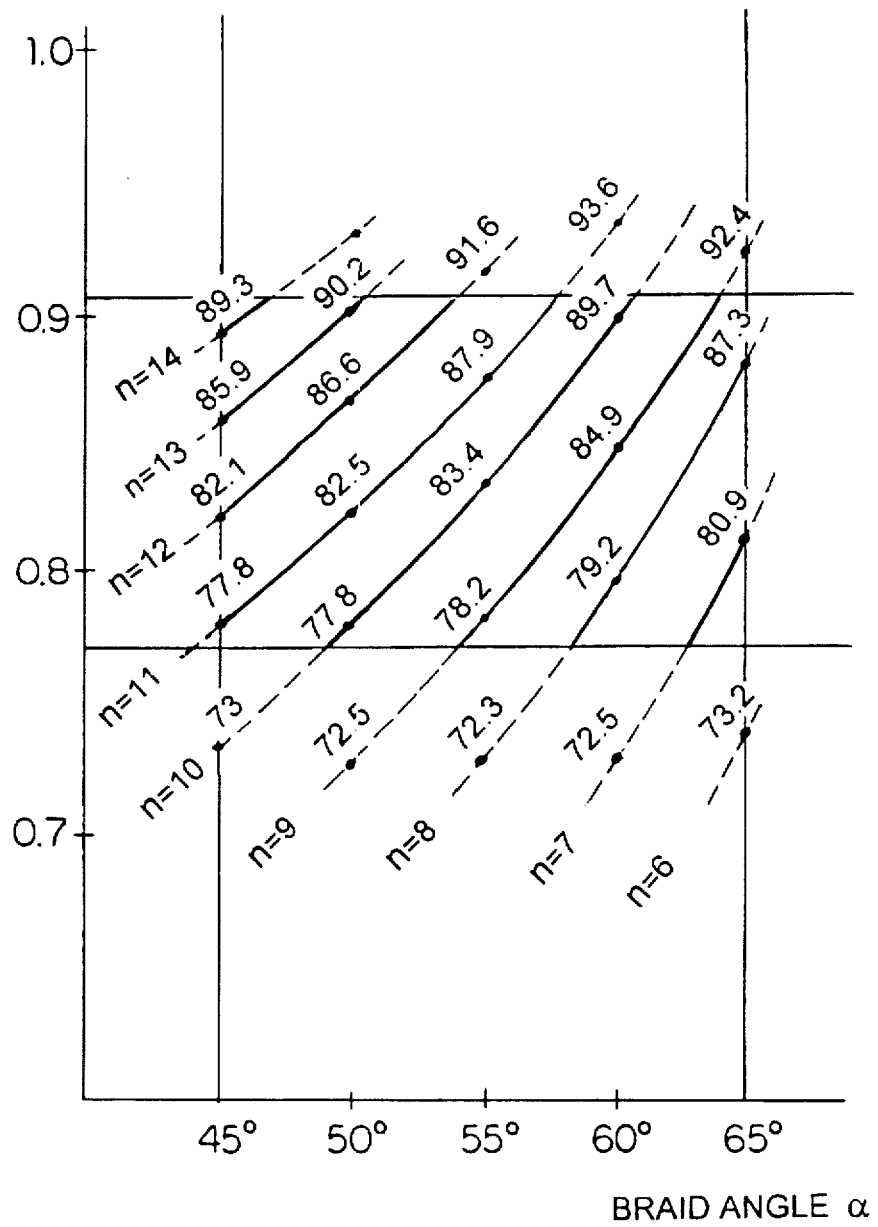
FIG. 23 is a graph showing the relationships among a braid density, a braid angle α and the number n of strands contained in one strand bundle in an eighteenth embodiment of a flexible tube for an endoscope.

FIG. 23 shows a a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 6 mm, 16 and 0.08 mm, respectively. As can be understood from the graph shown in FIG. 23, the number "n" which satisfies both the aforementioned conditions "45°≦α≦65°" and "0.772≦K≦0.906" must lie in a range of "7≦n≦14".

[Embodiment 19]

Figure 24:
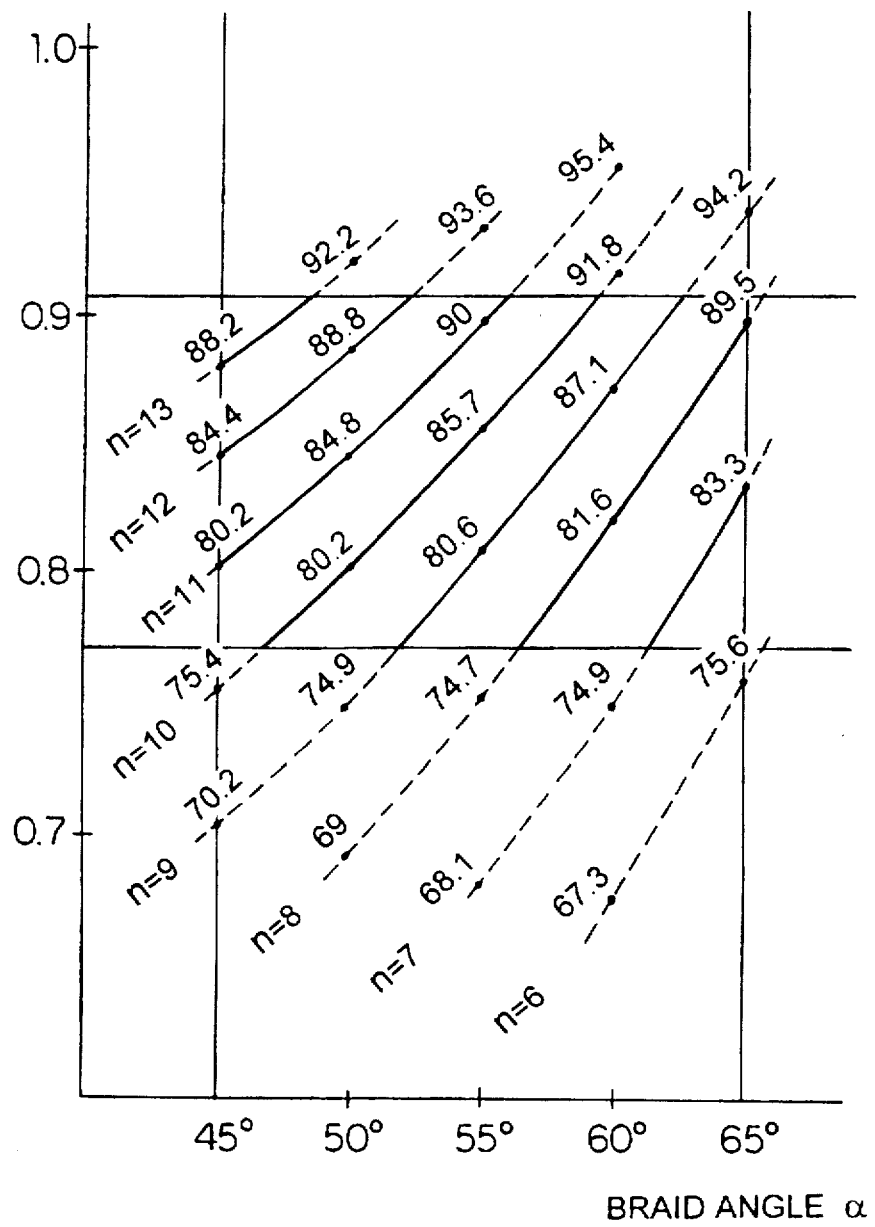
FIG. 24 is a graph showing the relationships among a braid density, a braid angle α and the number n of strands contained in one strand bundle in a nineteenth embodiment of a flexible tube for an endoscope.

FIG. 24 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 5 mm, 16 and 0.07 mm, respectively. As can be understood from the graph shown in FIG. 24, the number "n" which satisfies both the aforementioned conditions "45°≦α≦65°" and "0.772≦K≦0.906" must lie in a range of "7≦n≦13".

[Embodiment 20]

Figure 25:
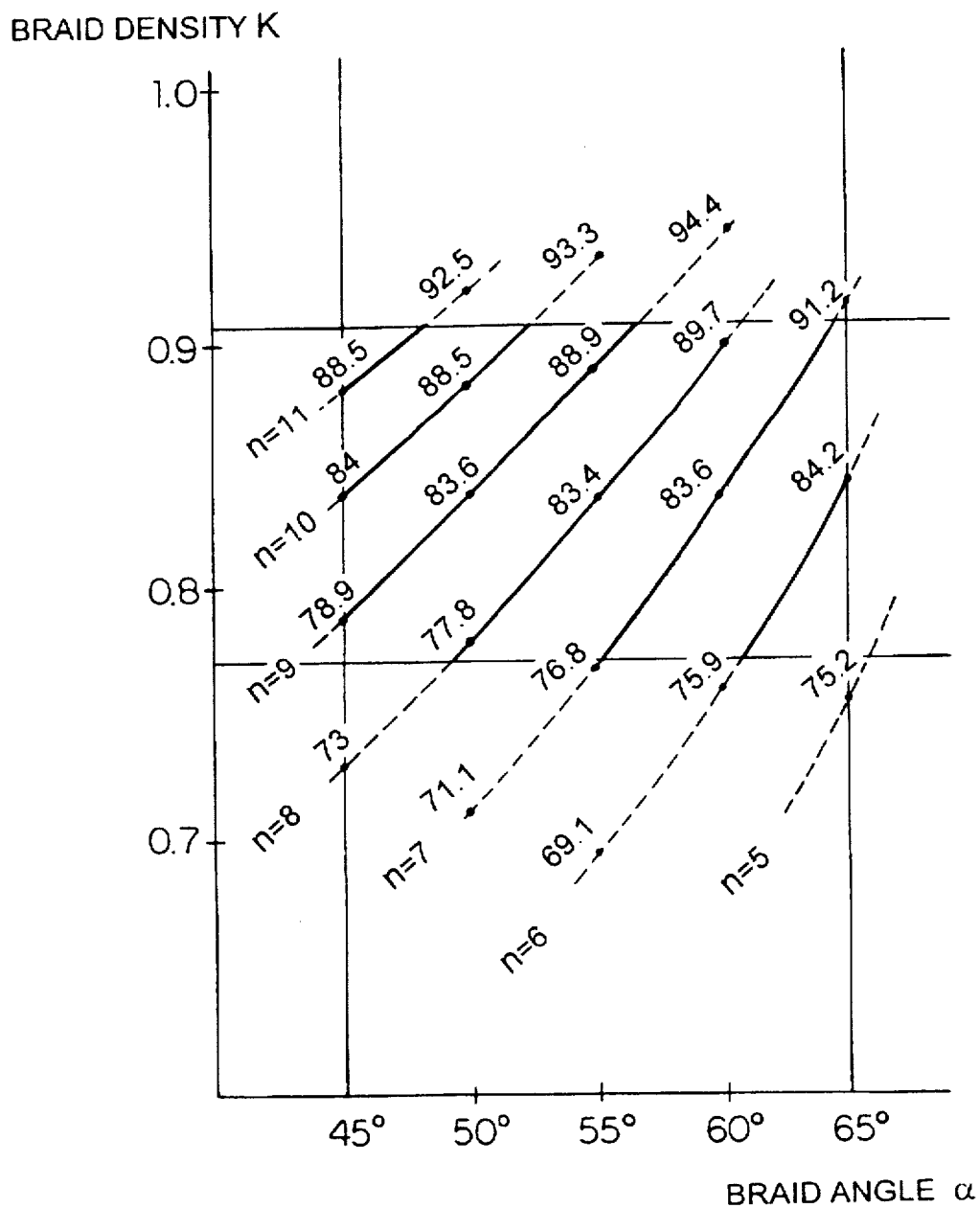
FIG. 25 is a graph showing the relationships among a braid density, a braid angle α and the number n of strands contained in one strand bundle in a twentieth embodiment of a flexible tube for an endoscope.

FIG. 25 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 3 mm, 16 and 0.05 mm, respectively. As can be understood from the graph shown in FIG. 25, the number "n" which satisfies both the aforementioned conditions "45°≦α≦65°" and "0.772≦K≦0.906" must lie in a range of "6≦n≦11".

[Embodiment 21]

Figure 26:
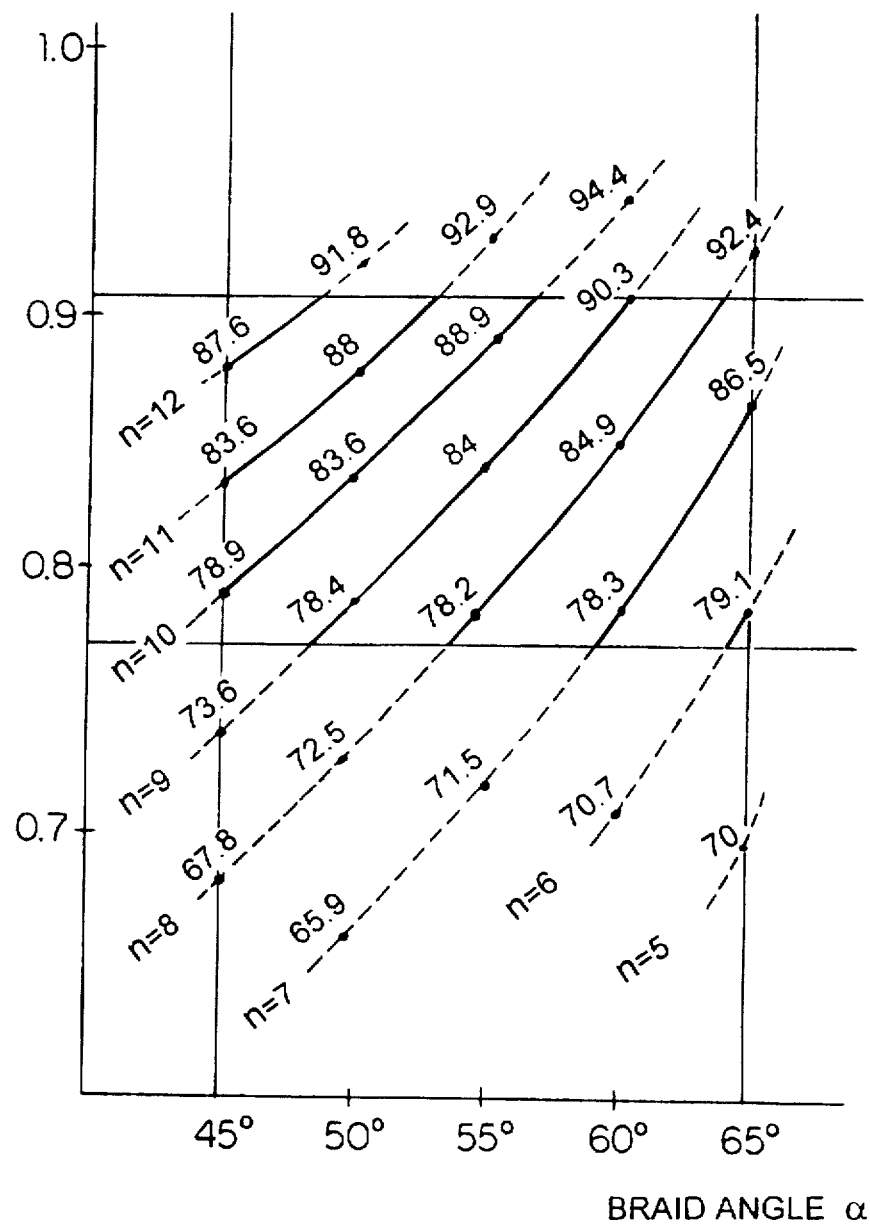
FIG. 26 is a graph showing the relationships among a braid density, a braid angle α and the number n of strands contained in one strand bundle in a twenty-first embodiment of a flexible tube for an endoscope.

FIG. 26 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 2 mm, 16 and 0.03 mm, respectively. As can be understood from the graph shown in FIG. 26, the number "n" which satisfies both the aforementioned conditions "45°≦α≦65°" and "0.772≦K≦0.906" must lie in a range of "6≦n≦12".

[Embodiment 22]

Figure 27:
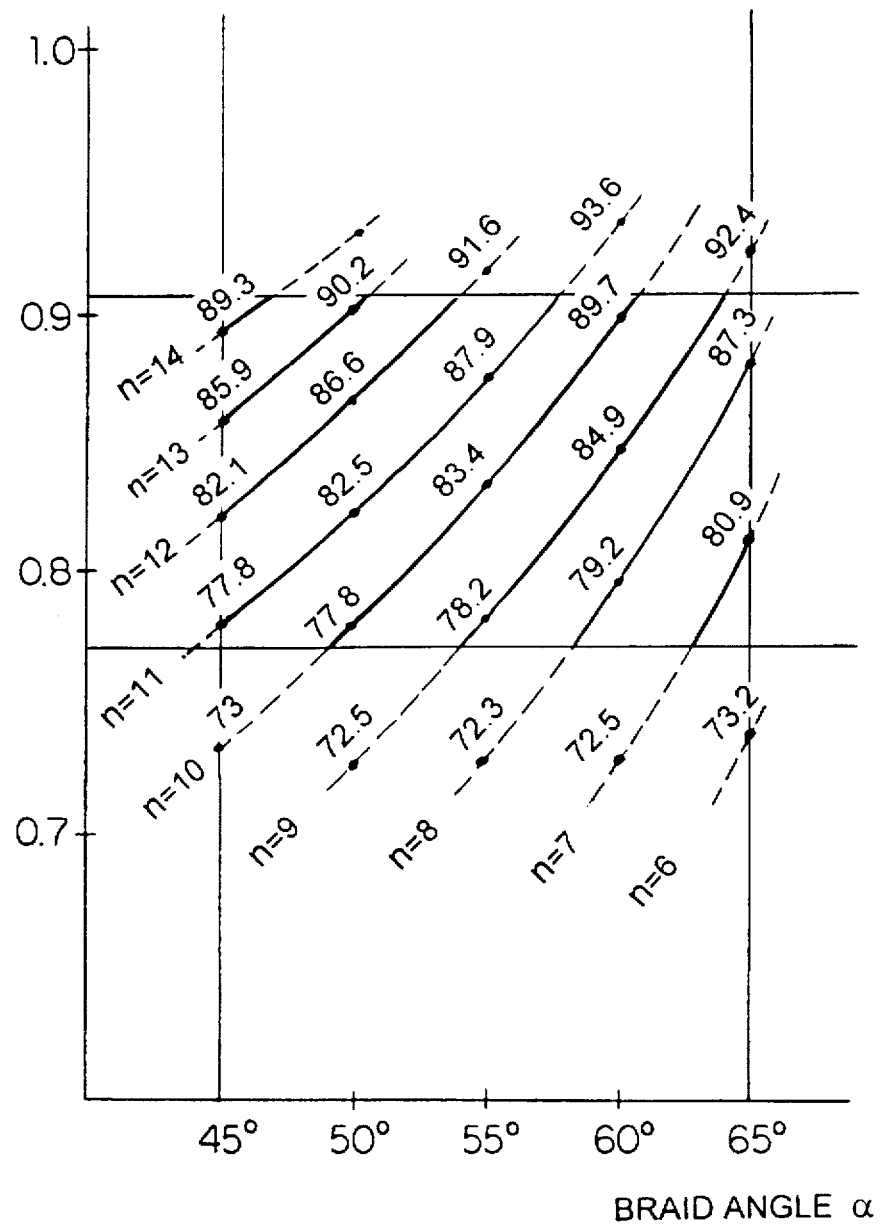
FIG. 27 is a graph showing the relationships among a braid density, a braid angle α and the number n of strands contained in one strand bundle in a twenty-second embodiment of a flexible tube for an endoscope.

FIG. 27 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 1.5 mm, 16 and 0.02 mm, respectively. As can be understood from the graph shown in FIG. 27, the number "n" which satisfies both the aforementioned conditions "45°≦α≦65°" and "0.772≦K≦0.906" must lie in a range of "7≦n≦14".

As can be understood from the foregoing, according to any one of the sixteenth through twenty-second embodiments, in the netted tube having sixteen strand bundles to be braided, since the number of strands contained in one strand bundle with respect to the average diameter of the netted tube is determined within a predetermined range, both the aforementioned conditions "45°≦α≦65°" and "0.772≦K≦0.906" can be satisfied. Thus, once a netted tube, made according to any one of the sixteenth through twenty-second embodiments, is combined with the flexible tube of an endoscope, a high bonding strength between the netted tube and the flexible jacket can be attained and the flexible tube can be smoothly bent. Therefore, the durability of the flexible tube greatly increases.

Twenty-third through twenty-sixth embodiments will be hereinafter discussed with reference to FIGS. 28 through 31. The twenty-third through twenty-sixth embodiments are similar to the sixth through ninth embodiments except that the number of strand bundles to be braided "m" is fixed to be 8 (m =8).

Therefore, by incorporating the aforementioned condition "0.772≦K≦0.906" obtained in the first through fifth embodiments, the value of "F" obtained according to the above relationship ①, and the aforementioned condition "45°≦α≦65°" into the above relationship ④, the number "n" of strands contained in one strand bundle 21 with respect to the average diameter of the netted tube 20 of the flexible tube 1 in the twenty-third through twenty-sixth embodiments can be determined as follows:

8.67 D≦n≦19.24 D when dw is equal to 0.02 mm,
5.78 D≦n≦12.82 D when dw is equal to 0.03 mm,
4.34 D≦n≦9.62 D when dw is equal to 0.04 mm,
3.47 D≦n≦7.69 D when dw is equal to 0.05 mm,
2.89 D≦n≦6.41 D when dw is equal to 0.06 mm,
2.48 D≦n≦5.49 D when dw is equal to 0.07 mm, and
2.17 D≦n≦4.81 D when dw is equal to 0.08 mm, wherein "n" is an integral number because of its nature.

As above-mentioned, it is preferable that the number "n" should be less than thirteen (i.e., 1≦n≦12). Due to this reason, it is preferable that the maximum value of the average diameter "D" of the netted tube 20 of the flexible tube 1 in the twenty-third through twenty-sixth embodiments with respect to the diameter "dw" of a strand in each strand bundle 21 should satisfy the following conditions:

$D \leq 1.38$ mm when dw is equal to 0.02 mm, $D \leq 2.07$ mm when dw is equal to 0.03 mm, $D \leq 2.76$ mm when dw is equal to 0.04 mm, $D \leq 3.45$ mm when dw is equal to 0.05 mm, $D \leq 4.15$ mm when dw is equal to 0.06 mm, $D \leq 4.83$ mm when dw is equal to 0.07 mm, and $D \leq 5.52$ mm when dw is equal to 0.08 mm.

[Embodiment 23]

Figure 28:
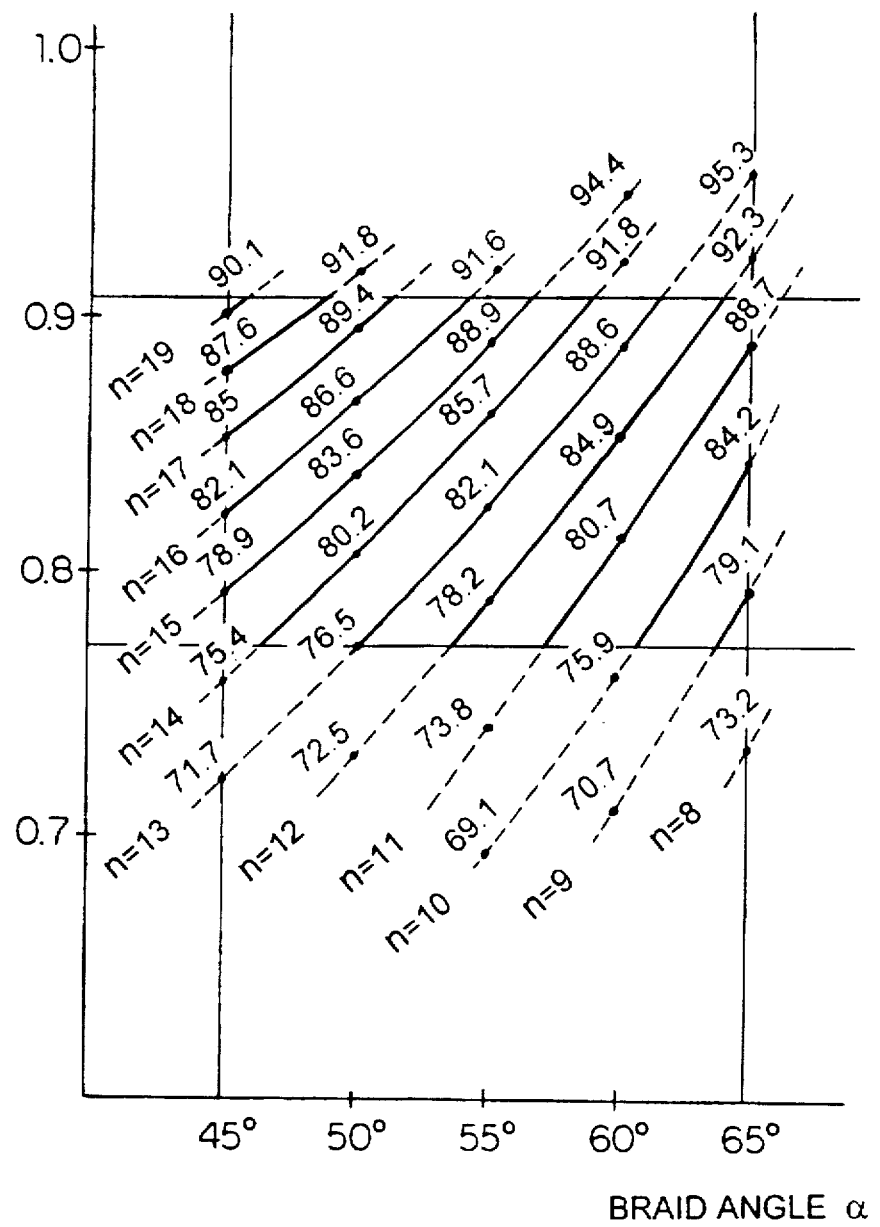
FIG. 28 is a graph showing the relationships among a braid density, a braid angle α and the number n of strands contained in one strand bundle in a twenty-third embodiment of a flexible tube for an endoscope.

FIG. 28 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 4 mm, 8 and 0.08 mm, respectively. As can be understood from the graph shown in FIG. 28, the number "n" which satisfies both the aforementioned conditions "$45° \leq \alpha \leq 65°$" and "$0.772 \leq K \leq 0.906$" must lie in a range of "$9 \leq n \leq 19$".

[Embodiment 24]

Figure 29:
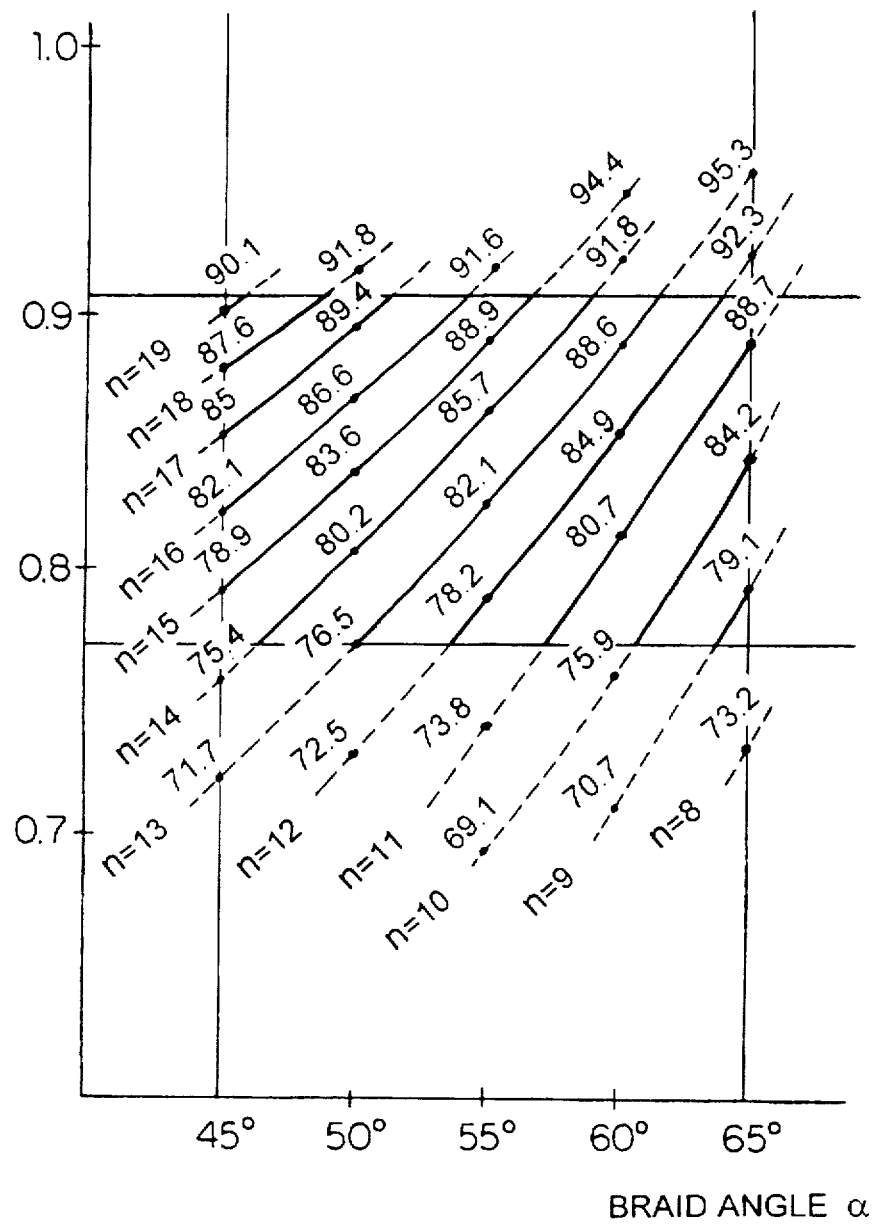
FIG. 29 is a graph showing the relationships among a braid density, a braid angle α and the number n of strands contained in one strand bundle in a twenty-fourth embodiment of a flexible tube for an endoscope.

FIG. 29 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 3 mm, 8 and 0.06 mm, respectively. As can be understood from the graph shown in FIG. 29, the number "n" which satisfies both the aforementioned conditions "$45° \leq \alpha \leq 65°$" and "$0.772 \leq K \leq 0.906$" must lie in a range of "$9 \leq n \leq 19$".

[Embodiment 25]

Figure 30:
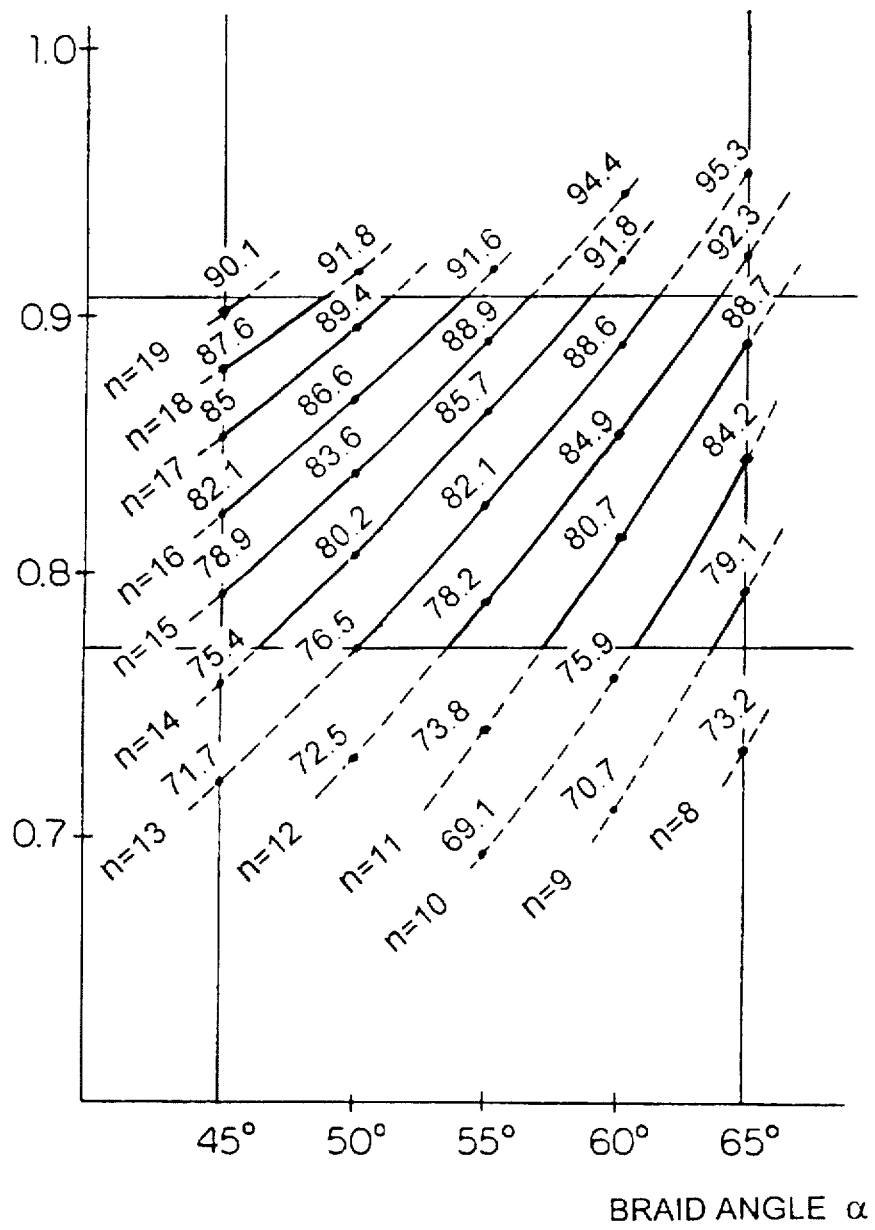
FIG. 30 is a graph showing the relationships among a braid density, a braid angle α and the number n of strands contained in one strand bundle in a twenty-fifth embodiment of a flexible tube for an endoscope.

FIG. 30 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 2 mm, 8 and 0.04 mm, respectively. As can be understood from the graph shown in FIG. 30, the number "n" which satisfies both the aforementioned conditions "$45° \leq \alpha \leq 65°$" and "$0.772 \leq K \leq 0.906$" must lie in a range of "$9 \leq n \leq 19$".

[Embodiment 26]

Figure 31:
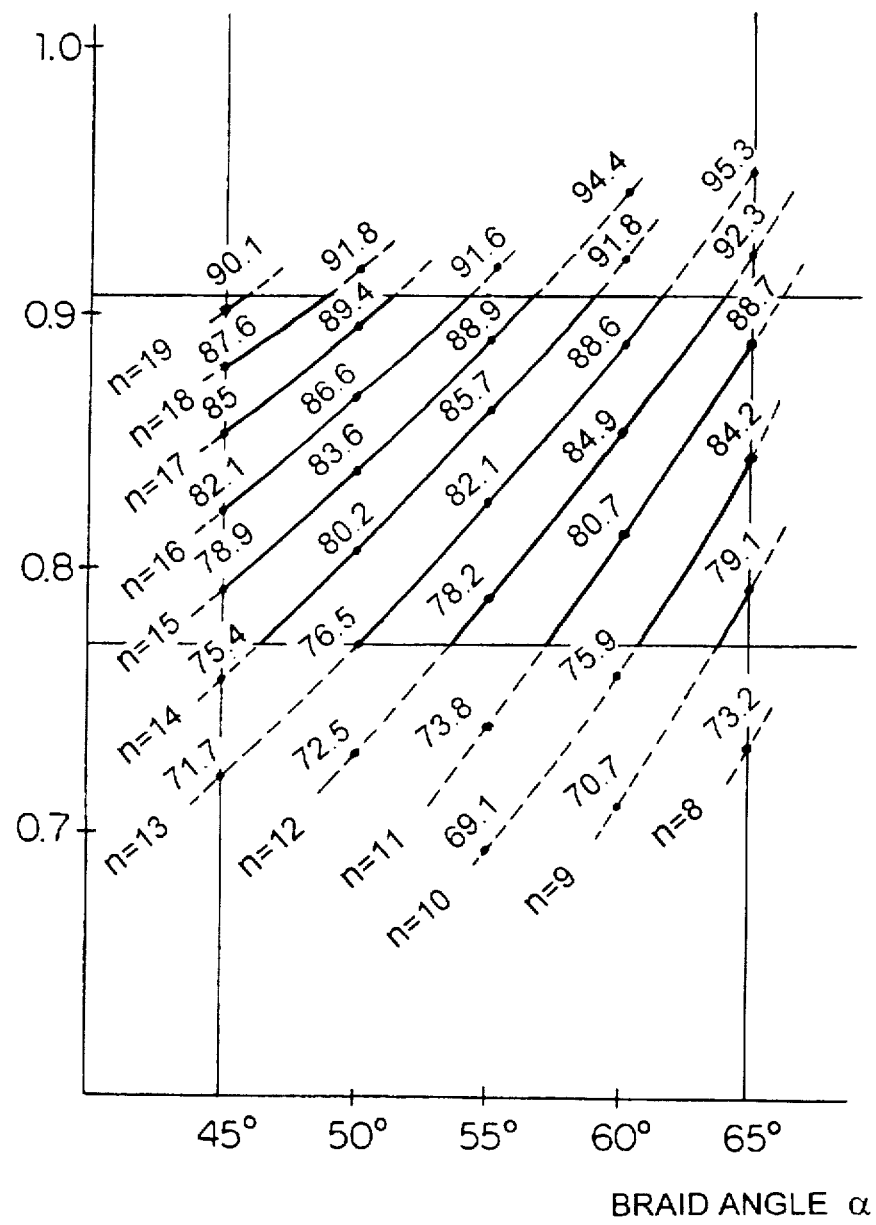
FIG. 31 is a graph showing the relationships among a braid density, a braid angle α and the number n of strands contained in one strand bundle in a twenty-sixth embodiment of a flexible tube for an endoscope.
Figure 36:
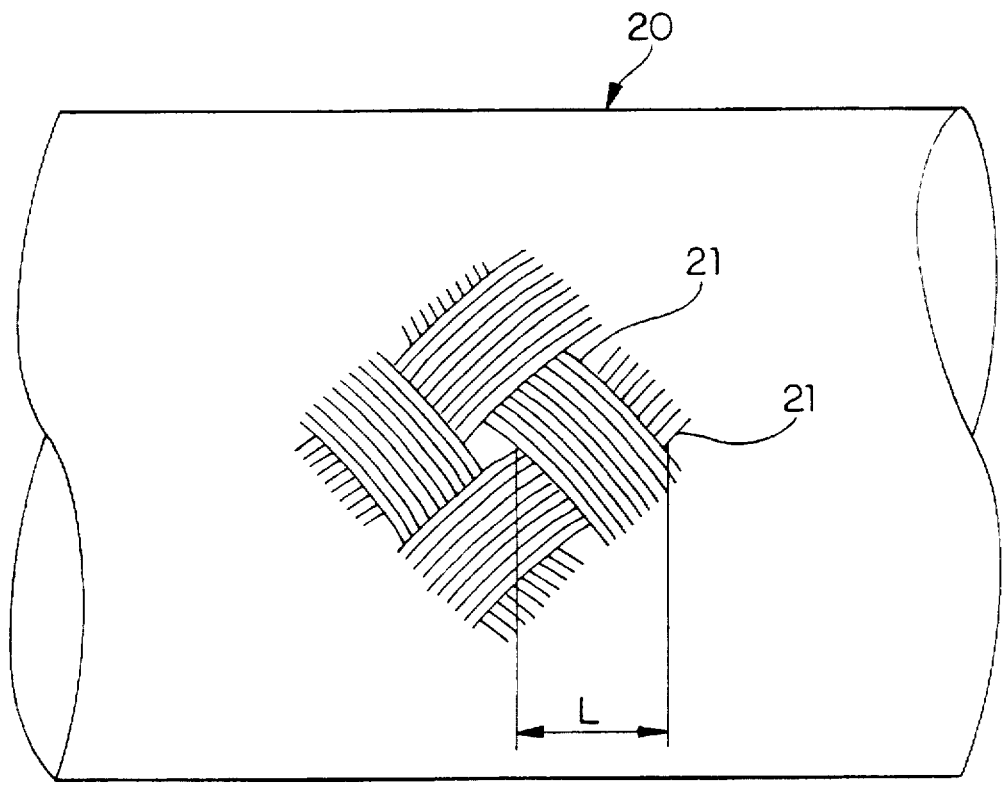
FIG. 36 is a partial side view of a netted tube.

FIG. 31 shows a graph showing the relationships among the braid density K (vertical axis), the braid angle α (horizontal axis) and the number n of strands contained in one strand bundle 21 under the condition that the average diameter of the netted tube "D", the number of strand bundles to be braided "m" and the diameter of a strand in each strand bundle "dw" are 1 mm, 8 and 0.02 mm, respectively. As can be understood from the graph shown in FIG. 31, the number "n" which satisfies both the aforementioned conditions "$45° \leq \alpha \leq 65°$" and "$0.772 \leq K \leq 0.906$" must lie in a range of "$9 \leq n \leq 19$".

As can be understood from the foregoing, according to any one of the twenty-third through twenty-sixth embodiments, in the netted tube having eight strand bundles to be braided, since the number of strands contained in one strand bundle with respect to the average diameter of the netted tube is determined within a predetermined range, both the aforementioned conditions "$45° \leq \alpha \leq 65°$" and "$0.772 \leq K \leq 0.906$" can be satisfied. Thus, once a netted tube, made according to any one of the twenty-third through twenty-sixth embodiments, is combined with the flexible tube of an endoscope, a high bonding strength between the netted tube and the flexible jacket can be attained and the flexible tube can be smoothly bent. Therefore, the durability of the flexible tube greatly increases.

In each of the sixth through twenty-sixth embodiments, each of the plurality of strand bundles 21 consists of a plurality of strands consisting of metal fine wires of a stainless steel, a copper alloy, tungsten steel or the like arranged in parallel, as noted above. However, in each of the sixth through twenty-sixth embodiments, the plurality of strands may instead consist of a mixture of the metal fine wires and non-metal fine wires arranged in parallel. The non-metal fine wires may be made of polyester fibers, nylon fibers, carbon fibers, etc.

Twenty-seventh through thirtieth embodiments will be hereinafter discussed with reference to FIGS. 32 through 35. The overall structure of the endoscope in each of the twenty-seventh through thirtieth embodiments is identical to that shown in FIG. 2. The twenty-seventh through thirtieth embodiments are similar to the first through fifth embodiments except that in the first through fifth embodiments each of the plurality of strand bundles 21 consists of a plurality of strands consisting of only metal fine wires arranged in parallel, whereas in the twenty-seventh through thirtieth embodiments each of the plurality of strand bundles 21 consists of a plurality of strands consisting of a mixture of the metal fine wires and non-metal fine wires arranged in parallel, and that the braid density K of the netted tube 20 is arranged to be within an approximate range of $0.79 \leq K \leq 0.90$, specifically, within a range of $0.788 \leq K \leq 0.906$. The non-metal fine wires may be made of polyester fibers, nylon fibers, carbon fibers, etc.

As the number of metal fine wires contained in a strand bundle increases, the mechanical strength of the flexible tube 1 increases. As the number of non-metal fine wires contained in a strand bundle increases, the bonding strength between the netted tube 20 and the flexible jacket 30 increases. Due to these reasons, the ratio of the number of metal fine wires to the number of non-metal wires may be determined depending upon the usage of the flexible tube 1 or the like.

In the twenty-seventh through thirtieth embodiments, after the spiral tube 10 has been covered with the netted tube 20, the outer surface of the netted tube 20 is covered by the flexible jacket 30 using one of the aforementioned two processing methods. In each of the twenty-seventh through thirtieth embodiments (described later), it was found that the flexible jackets prepared by both methods shared a similar bonding strength.

[Embodiment 27]

FIG. 32 is a table showing details regarding the twenty-seventh embodiment. In the twenty-seventh embodiment, five types of flexible tube 1 (1)–(5) having different strand diameters and different numbers of strands in one bundle (n) of the netted tube 20 were prepared and evaluated for use as a flexible tube for an endoscope for the colon. The outer diameter of the five types of flexible tube 1 of the twenty-seventh embodiment was approximately 13 mm. The strands of the netted tube 20 were formed of stainless steel wires and polyester fibers, each wire or fiber having a diameter of 0.1 mm.

In the case of type (1) of the present embodiment, having a braid density K of 0.715, while the flexible jacket 30 is highly permeable into the mesh of the netted tube 20, thus providing a good bonding property between the netted tube 20 and the flexible jacket 30, the flexible jacket 30 penetrates up until the spiral tube 10. This results in making bending difficult, and so the flexible tube 1 cannot be used for an endoscope.

In the cases of types (2) and (3) of the present embodiment, having a braid density K of 0.792 and 0.857, respectively, after cutting the flexible tube 1, a visual inspection of the inside of the flexible tube 1 revealed that the flexible jacket 30 penetrated into the netted tube 20, and that the bonding strength between the flexible jacket 30 and the netted tube 20 was sufficient to pass the peeling test.

In the case of type (4) of the present embodiment, having a braid density K of 0.91, while the flexible jacket 30 slightly penetrates into the netted tube 20, the amount of penetration was small so that the bonding strength between the netted tube 20 and the jacket 30 was somewhat poor.

In the case of type (5) of the present embodiment, having a braid density K of 0.951, since the flexible jacket 30 did not penetrate into the netted tube 20, but remained on the outer surface, the bonding strength was poor. Therefore, in the case of type (5), if the flexible tube 1 is bent by an amount having a small radius of curvature, the flexible jacket 30 can easily separate from the netted tube 20, thus causing creasing to occur.

[Embodiment 28]

FIG. 33 is a table showing details regarding the twenty-eighth embodiment. In the twenty-eighth embodiment, five types of flexible tube 1 (1)–(5) each having different strand diameters and different numbers of strands in one bundle (n) of the netted tube 20 were prepared and evaluated for use as a flexible tube for an endoscope for the upper alimentary canal. The outer diameter of the five types of flexible tube 1 of the twenty-eighth embodiment was approximately 9 mm. The strands of the netted tube 20 were formed of stainless steel wires and polyester fibers, each wire or fiber having a diameter of 0.08 mm.

For this twenty-eighth embodiment and subsequent embodiments (i.e., twenty-ninth through thirtieth embodiments) having a flexible tube 1 having a relatively small outer diameter (compared with the twenty-seventh embodiment), since linear peeling conditions cannot be attained if the flexible jacket 30 is slit with a 5 mm interval, and since a part of the flexible jacket 30 is often torn off if the flexible jacket 30 is slit and stretched by less than a 5 mm interval, the peeling strength cannot be measured. Thus, in the following embodiments 29 through 30, bonding between the netted tube 20 and the flexible jacket 30 is determined from the penetration of the netted tube 20 into the flexible jacket 30.

The results obtained from the present embodiment showed that type (1) having a braid density K of 0.711 and type (5) having a braid density K of 0.948 were not acceptable, while type (2) having a braid density K of 0.788, type (3) having a braid density K of 0.853, and type (4) having a braid density K of 0.906, were acceptable.

[Embodiment 29]

FIG. 34 is a table showing the twenty-ninth embodiment. In the twenty-ninth embodiment, four types of flexible tube 1 (1)–(4) having different strand diameters and different numbers of strands in one bundle (n) of the netted tube 20 were prepared and evaluated for use as a flexible tube for an endoscope for the bronchus. The outer diameter of the four types of flexible tube 1 of the twenty-ninth embodiment was approximately 6 mm. The strands of the netted tube 20 were formed of stainless steel wires and polyester fibers, each wire or fiber having a diameter of 0.08 mm.

The results obtained from the present embodiment showed that type (1) having a braid density K of 0.738 and type (4) having a braid density K of 0.952 were not acceptable, while type (2) having a braid density K of 0.829, and type (3) having a braid density K of 0.90 were acceptable.

[Embodiment 30]

FIG. 35 is a table showing details regarding the thirtieth embodiment. In, the thirtieth embodiment, six types of flexible tube 1 (1)–(6) having different strand diameters and different numbers of strands in one bundle (n) of the netted tube 20 were prepared and evaluated for use as a flexible tube for an endoscope for the bronchus or for otolaryngology. The outer diameter of the six types of flexible tube 1 of the thirtieth embodiment was approximately 3.5 mm. The strands of the netted tube 20 were formed of stainless steel wires and polyester fibers, each wire or fiber having a diameter of 0.03 mm.

The results obtained from the present embodiment showed that type (1) having a braid density K of 0.735, type (5) having a braid density K of 0.911, and type (6) having a braid density K of 0.94 were not acceptable, while type (2) having a braid density K of 0.788, type (3) having a braid density K of 0.835, and type (4) having a braid density K of 0.876 were acceptable.

Each of the above twenty-seventh through thirtieth embodiments was tested using strands formed of copper alloy wires and polyester fibers for the netted tube 20. The results obtained showed no significant difference from the results of the embodiments using strands formed of stainless steel and polyester fibers.

According to any one of the twenty-seventh through thirtieth embodiments, since high bonding strength can be obtained between the netted tube and the flexible jacket when the braid density K is arranged to be less than or equal to 0.906 ($K \leq 0.906$), creases hardly occur, even if the flexible tube is bent by an amount having a small radius of curvature. In addition, since the braid density K is arranged to be greater than or equal to 0.788 ($0.788 \leq K$), the flexible jacket does not bind to the spiral tube, and thus the flexible tube can be smoothly bent and has a good insertion capability for insertion into a body cavity.

The present invention may be applied to a flexible tube, having a different structure from that of the flexible tube 1 shown in FIG. 1, in which a plurality of the spiral tubes 10 and a plurality of the netted tubes 20 are alternately arranged to cover over one another.

It should be understood that while the present invention is applied to the flexible tube 1, the present invention may also be equally applied to the connection cord 6, by applying the above-mentioned structure to the connection cord 6.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A flexible tube for an endoscope, comprising:
   a spiral tube;
   a netted tube covering an outer surface of said spiral tube, said netted tube being formed by braiding a plurality of strand bundles each formed by closely arranging a plurality of fine wires in parallel; and
   a jacket made of a flexible synthetic resin which covers an outer surface of said netted tube;
   wherein a braid density K of said netted tube lies in a range of $0.772 \leq K \leq 0.906$;

wherein K=(S−s)/S;

wherein "S" is an area of an intersection of two strand bundles in union with an area of a gap between said intersecting strand bundles and neighboring strand bundles of one side of said intersecting strand bundles, the widths of said area "S" being substantially equal; and wherein "s" is the area of the gap produced by the intersecting strand bundles, wherein no strands are covered, the widths of said area "s" being substantially equal.

2. The flexible tube according to claim 1, wherein said jacket is formed by dissolving a synthetic resin in a solvent and applying a resultant material to said outer surface of said netted tube.

3. The flexible tube according to claim 1, wherein said jacket is formed by heating a thermoplastic synthetic resin at a temperature higher than a softening point of said thermoplastic synthetic resin, so that said thermoplastic synthetic resin penetrates gaps formed in said netted tube from outside said netted tube.

4. The flexible tube according to claim 1, wherein said jacket comprises a synthetic resin consisting of a polyurethane elastomer.

5. The flexible tube according to claim 1, wherein said jacket is formed by firstly covering said netted tube with a synthetic resin formed in a tubular shape, and secondly by heating said synthetic resin at a temperature higher than a softening point of said synthetic resin, so that said synthetic resin penetrates gaps formed in said netted tube from outside said netted tube.

6. The flexible tube according to claim 1, wherein said plurality of fine wires are each made of metal.

7. The flexible tube according to claim 6, wherein said plurality of fine wires are each made of a stainless steel.

8. The flexible tube according to claim 6, wherein said plurality of fine wires are each made of a copper alloy.

9. The flexible tube according to claim 6, wherein said plurality of fine wires are each made of a tungsten steel.

10. The flexible tube according to claim 1, wherein the following relationships are satisfied:

$$45° \leq \alpha \leq 65°,$$

and $$n=24,$$

wherein "α" represents a braid angle and "n" represents a number of strands contained in one of said plurality of strand bundles, and further wherein said number "n" satisfies all the following relationships:

2.89 D≦n≦6.41 D when dw is equal to 0.02 mm,
1.93 D≦n≦4.27 D when dw is equal to 0.03 mm,
1.45 D≦n≦3.20 D when dw is equal to 0.04 mm,
1.16 D≦n≦2.56 D when dw is equal to 0.05 mm,
0.97 D≦n≦2.13 D when dw is equal to 0.06 mm,
0.83 D≦n≦1.83 D when dw is equal to 0.07 mm,
0.73 D≦n≦1.60 D when dw is equal to 0.08 mm,
0.65 D≦n≦1.42 D when dw is equal to 0.09 mm,
0.58 D≦n≦1.28 D when dw is equal to 0.10 mm, and
0.49 D≦n≦1.06 D when dw is equal to 0.12 mm, wherein "dw" represents a diameter of a strand of each strand bundle in said plurality of strand bundles and "D" represents an average diameter of said netted tube.

11. The flexible tube according to claim 10, wherein a maximum value of said average diameter "D" satisfies all the following relationships:

1.9 mm≦D≦4.1 mm when dw is equal to 0.02 mm,
2.9 mm≦D≦6.2 mm when dw is equal to 0.03 mm,
3.8 mm≦D≦8.2 mm when dw is equal to 0.04 mm,
4.7 mm≦D≦10.3 mm when dw is equal to 0.05 mm,
5.7 mm≦D≦12.3 mm when dw is equal to 0.06 mm,
6.6 mm≦D≦14.4 mm when dw is equal to 0.07 mm,
7.5 mm≦D≦16.4 mm when dw is equal to 0.08 mm,
8.5 mm≦D≦18.4 mm when dw is equal to 0.09 mm,
9.4 mm≦D≦20.6 mm when dw is equal to 0.10 mm, and
11.4 mm≦D≦24.4 mm when dw is equal to 0.12 mm.

12. The flexible tube according to claim 10, wherein said plurality of fine wires are each made of metal.

13. The flexible tube according to claim 12, wherein said plurality of fine wires are each made of a stainless steel.

14. The flexible tube according to claim 12, wherein said plurality of fine wires are each made of a copper alloy.

15. The flexible tube according to claim 12, wherein said plurality of fine wires are each made of a tungsten steel.

16. The flexible tube according to claim 10, wherein said plurality of fine wires comprise metal fine wires and non-metal fine wires.

17. The flexible tube according to claim 16, wherein said non-metal fine wires are made of polyester fibers.

18. The flexible tube according to claim 16, wherein said non-metal fine wires are made of nylon fibers.

19. The flexible tube according to claim 16, wherein said non-metal fine wires are made of carbon fibers.

20. The flexible tube according to claim 1, wherein the following relationships are satisfied:

$$45° \leq \alpha \leq 65°,$$

and $$n=32,$$

wherein "α" represents a braid angle and "n" represents a number of strands contained in one of said plurality of strand bundles, and further wherein said number "n" satisfies all the following relationships:

2.17 D≦n≦4.81 D when dw is equal to 0.02 mm,
1.45 D≦n≦3.20 D when dw is equal to 0.03 mm,
1.09 D≦n≦2.40 D when dw is equal to 0.04 mm,
0.87 D≦n≦1.92 D when dw is equal to 0.05 mm,
0.73 D≦n≦1.60 D when dw is equal to 0.06 mm,
0.62 D≦n≦1.37 D when dw is equal to 0.07 mm,
0.55 D≦n≦1.20 D when dw is equal to 0.08 mm,
0.49 D≦n≦1.06 D when dw is equal to 0.09 mm,
0.44 D≦n≦0.96 D when dw is equal to 0.10 mm, and
0.37 D≦n≦0.80 D when dw is equal to 0.12 mm, wherein "dw" represents a diameter of a strand of each strand bundle in said plurality of strand bundles and "D" represents an average diameter of said netted tube.

21. The flexible tube according to claim 20, wherein a maximum value of said average diameter "D" satisfies all the following relationships:

2.5 mm≦D≦5.5 mm when dw is equal to 0.02 mm,
3.8 mm≦D≦8.2 mm when dw is equal to 0.03 mm,
5.0 mm≦D≦11.0 mm when dw is equal to 0.04 mm,
6.3 mm≦D≦13.7 mm when dw is equal to 0.05 mm,
7.5 mm≦D≦16.4 mm when dw is equal to 0.06 mm,
8.8 mm≦D≦19.3 mm when dw is equal to 0.07 mm,
10.0 mm≦D≦21.8 mm when dw is equal to 0.08 mm, 11.4 mm≦D≦24.4 mm when dw is equal to 0.09 mm, 12.5 mm≦D≦27.2 mm when dw is equal to 0.10 mm, and 15.0 mm≦D≦32.4 mm when dw is equal to 0.12 mm.

22. The flexible tube according to claim 20, wherein said plurality of fine wires are each made of metal.

23. The flexible tube according to claim 22, wherein said plurality of fine wires are each made of a stainless steel.

24. The flexible tube according to claim 22, wherein said plurality of fine wires are each made of a copper alloy.

25. The flexible tube according to claim 22, wherein said plurality of fine wires are each made of a tungsten steel.

26. The flexible tube according to claim 20, wherein said plurality of fine wires comprise metal fine wires and non-metal fine wires.

27. The flexible tube according to claim 26, wherein said non-metal fine wires are made of polyester fibers.

28. The flexible tube according to claim 26, wherein said non-metal fine wires are made of nylon fibers.

29. The flexible tube according to claim 26, wherein said non-metal fine wires are made of carbon fibers.

30. The flexible tube according to claim 1, wherein said flexible tube satisfies the following relationships:

$$45° \leq \alpha \leq 65°,$$

and $$n=16,$$

wherein "α" represents a braid angle and "n" represents a number of strands contained in one of said plurality of strand bundles, and further wherein said number "n" satisfies all the following relationships:

4.34 D≦n≦9.62 D when dw is equal to 0.02 mm,
2.89 D≦n≦6.41 D when dw is equal to 0.03 mm,
2.17 D≦n≦4.81 D when dw is equal to 0.04 mm,
1.74 D≦n≦3.84 D when dw is equal to 0.05 mm,
1.45 D≦n≦3.20 D when dw is equal to 0.06 mm,
1.24 D≦n≦2.74 D when dw is equal to 0.07 mm,
1.09 D≦n≦2.40 D when dw is equal to 0.08 mm,
0.97 D≦n≦2.13 D when dw is equal to 0.09 mm,
0.87 D≦n≦1.92 D when dw is equal to 0.10 mm, and
0.73 D≦n≦1.60 D when dw is equal to 0.12 mm, wherein "dw" represents a diameter of a strand of each strand bundle in said plurality of strand bundles and "D" represents an average diameter of said netted tube.

31. The flexible tube according to claim 30, wherein a maximum value of said average diameter "D" satisfies all the following relationships:

1.25 mm≦D≦2.76 mm when dw is equal to 0.02 mm,
1.88 mm≦D≦4.15 mm when dw is equal to 0.03 mm,
2.5 mm≦D≦5.5 mm when dw is equal to 0.04 mm,
3.2 mm≦D≦6.8 mm when dw is equal to 0.05 mm,
3.8 mm≦D≦8.2 mm when dw is equal to 0.06 mm,
4.4 mm≦D≦9.6 mm when dw is equal to 0.07 mm,
5 mm≦D≦11 mm when dw is equal to 0.08 mm,
5.7 mm≦D≦12.3 mm when dw is equal to 0.09 mm,
6.3 mm≦D≦13.7 mm when dw is equal to 0.10 mm, and
7.5 mm≦D≦16.4 mm when dw is equal to 0.12 mm.

32. The flexible tube according to claim 30, wherein said plurality of fine wires are each made of metal.

33. The flexible tube according to claim 32, wherein said plurality of fine wires are each made of a stainless steel.

34. The flexible tube according to claim 32, wherein said plurality of fine wires are each made of a copper alloy.

35. The flexible tube according to claim 32, wherein said plurality of fine wires are each made of a tungsten steel.

36. The flexible tube according to claim 30, wherein said plurality of fine wires comprise metal fine wires and non-metal fine wires.

37. The flexible tube according to claim 36, wherein said non-metal fine wires are made of polyester fibers.

38. The flexible tube according to claim 36, wherein said non-metal fine wires are made of nylon fibers.

39. The flexible tube according to claim 36, wherein said non-metal fine wires are made of carbon fibers.

40. The flexible tube according to claim 1, wherein said flexible tube satisfies all the following relationships:

$$45° \leq \alpha \leq 65°,$$

and $$n=8,$$

wherein "α" represents a braid angle and "n" represents a number of strands contained in one of said plurality of strand bundles, and further wherein said number "n" satisfies all the following relationships:

8.67 D≦n≦19.24 D when dw is equal to 0.02 mm,
5.78 D≦n≦12.82 D when dw is equal to 0.03 mm,
4.34 D≦n≦9.62 D when dw is equal to 0.04 mm,
3.47 D≦n≦7.69 D when dw is equal to 0.05 mm,
2.89 D≦n≦6.41 D when dw is equal to 0.06 mm,
2.48 D≦n≦5.49 D when dw is equal to 0.07 mm, and
2.17 D≦n≦4.81 D when dw is equal to 0.08 mm, wherein "dw" represents a diameter of a strand of each strand bundle in said plurality of strand bundles and "D" represents an average diameter of said netted tube.

41. The flexible tube according to claim 40, wherein a maximum value of said average diameter "D" satisfies all the following relationships:

D≦1.38 mm when dw is equal to 0.02 mm,
D≦2.07 mm when dw is equal to 0.03 mm,
D≦2.76 mm when dw is equal to 0.04 mm,
D≦3.45 mm when dw is equal to 0.05 mm,
D≦4.15 mm when dw is equal to 0.06 mm,
D≦4.83 mm when dw is equal to 0.07 mm, and
D≦5.52 mm when dw is equal to 0.08 mm.

42. The flexible tube according to claim 40, wherein said plurality of fine wires are each made of metal.

43. The flexible tube according to claim 42, wherein said plurality of fine wires are each made of a stainless steel.

44. The flexible tube according to claim 42, wherein said plurality of fine wires are each made of a copper alloy.

45. The flexible tube according to claim 42, wherein said plurality of fine wires are each made of a tungsten steel.

46. The flexible tube according to claim 40, wherein said plurality of fine wires comprise metal fine wires and non-metal fine wires.

47. The flexible tube according to claim 46, wherein said non-metal fine wires are made of polyester fibers.

48. The flexible tube according to claim 46, wherein said non-metal fine wires are made of nylon fibers.

49. The flexible tube according to claim 46, wherein said non-metal fine wires are made of carbon fibers.

50. A flexible tube for an endoscope, comprising:
    a spiral tube;
    a netted tube covering an outer surface of said spiral tube, said netted tube being formed by braiding a plurality of strand bundles each formed by closely arranging a plurality of fine wires in parallel, said plurality of fine wires comprising at least one metal fine wire and at least one non-metal fine wire; and a jacket made of a flexible synthetic resin which covers an outer surface of said netted tube;

wherein a braid density K of said netted tube lies in a range of $0.788 \leq K \leq 0.906$;

wherein $K=(S-s)/S$;

wherein "S" is an area of an intersection of two strand bundles in union with an area of a gap between said intersecting strand bundles and neighboring strand bundles of one side of said intersecting strand bundles, the widths of said area "S" being substantially equal; and wherein "s" is the area of the gap produced by the intersecting strand bundles, wherein no strands are covered, the widths of said area "s" being substantially equal.

51. The flexible tube according to claim 50, wherein said jacket is formed by dissolving a synthetic resin in a solvent and applying a resultant material to said outer surface of said netted tube.

52. The flexible tube according to claim 50, wherein said jacket is formed by heating a thermoplastic synthetic resin at a temperature higher than a softening point of said thermoplastic synthetic resin, so that said thermoplastic synthetic resin penetrates gaps formed in said netted tube from outside said netted tube.

53. The flexible tube according to claim 50, wherein said jacket comprises a synthetic resin consisting of a polyurethane elastomer.

54. The flexible tube according to claim 50, wherein said jacket is formed by firstly covering said netted tube with a synthetic resin formed in a tubular shape, and secondly by heating said synthetic resin at a temperature higher than a softening point of said synthetic resin, so that said synthetic resin penetrates gaps formed in said netted tube from outside said netted tube.

55. The flexible tube according to claim 50, wherein said at least one metal fine wire is made of a stainless steel.

56. The flexible tube according to claim 50, wherein said at least one metal fine wire is made of a copper alloy.

57. The flexible tube according to claim 50, wherein said at least one metal fine wire is made of a tungsten steel.

58. The flexible tube according to claim 50, wherein said at least one non-metal fine wire is made of a polyester fiber.

59. The flexible tube according to claim 50, wherein said at least one non-metal fine wires are made of nylon fibers.

60. The flexible tube according to claim 50, wherein said at least one non-metal fine wires are made of carbon fibers.

61. A netted tube, formed by braiding a plurality of strand bundles each formed by closely arranging a plurality of fine wires in parallel, used in a flexible tube for an endoscope, said flexible tube comprising:

a spiral tube, said netted tube covering an outer surface of said spiral tube; and a jacket made of a flexible synthetic resin which covers an outer surface of said netted tube;

wherein the following relationships are satisfied:

$$45° \leq \alpha \leq 65°,$$

$$0.772 \leq K \leq 0.906$$

and $$n=24,$$

wherein "α" represents a braid angle, "K" represents a braid density, and "n" represents a number of strands contained in one of said plurality of strand bundles, and further wherein said number "n" satisfies all the following relationships:

2.89 D≤n≤6.41 D when dw is equal to 0.02 mm,
1.93 D≤n≤4.27 D when dw is equal to 0.03 mm,
1.45 D≤n≤3.20 D when dw is equal to 0.04 mm,
1.16 D≤n≤2.56 D when dw is equal to 0.05 mm,
0.97 D≤n≤2.13 D when dw is equal to 0.06 mm,
0.83 D≤n≤1.83 D when dw is equal to 0.07 mm,
0.73 D≤n≤1.60 D when dw is equal to 0.08 mm,
0.65 D≤n≤1.42 D when dw is equal to 0.09 mm,
0.58 D≤n≤1.28 D when dw is equal to 0.10 mm, and
0.49 D≤n≤1.06 D when dw is equal to 0.12 mm, wherein "dw" represents a diameter of a strand of each strand bundle in said plurality of strand bundles and "D" represents an average diameter of said netted tube;

wherein $K=(S-s)/S$;

wherein "S" is an area of an intersection of two strand bundles in union with an area of a gap between said intersecting strand bundles and neighboring strand bundles of one side of said intersecting strand bundles, the widths of said area "S" being substantially equal; and wherein "s" is the area of the gap produced by the intersecting strand bundles, wherein no strands are covered, the widths of said area "s" being substantially equal.

62. The netted tube according to claim 61, wherein a maximum value of said average diameter "D" satisfies all the following relationships:

1.9 mm≤D≤4.1 mm when dw is equal to 0.02 mm,
2.9 mm≤D≤6.2 mm when dw is equal to 0.03 mm,
3.8 mm≤D≤8.2 mm when dw is equal to 0.04 mm,
4.7 mm≤D≤10.3 mm when dw is equal to 0.05 mm,
5.7 mm≤D≤12.3 mm when dw is equal to 0.06 mm,
6.6 mm≤D≤14.4 mm when dw is equal to 0.07 mm,
7.5 mm≤D≤16.4 mm when dw is equal to 0.08 mm,
8.5 mm≤D≤18.4 mm when dw is equal to 0.09 mm,
9.4 mm≤D≤20.6 mm when dw is equal to 0.10 mm, and
11.4 mm≤D≤24.4 mm when dw is equal to 0.12 mm.

63. A netted tube, formed by braiding a plurality of strand bundles each formed by closely arranging a plurality of fine wires in parallel, used in a flexible tube for an endoscope, said flexible tube comprising:

a spiral tube, said netted tube covering an outer surface of said spiral tube; and a jacket made of a flexible synthetic resin which covers an outer surface of said netted tube;

wherein the following relationships are satisfied:

$$45° \leq \alpha \leq 65°,$$

$$0.772 \leq K \leq 0.906$$

and $$n=32,$$

wherein "α" represents a braid angle, "K" represents a braid density, and "n" represents a number of strands contained in one of said plurality of strand bundles, and further wherein said number "n" satisfies all the following relationships:

2.17 D≦n≦4.81 D when dw is equal to 0.02 mm,
1.45 D≦n≦3.20 D when dw is equal to 0.03 mm,
1.09 D≦n≦2.40 D when dw is equal to 0.04 mm,
0.87 D≦n≦1.92 D when dw is equal to 0.05 mm,
0.73 D≦n≦1.60 D when dw is equal to 0.06 mm,
0.62 D≦n≦1.37 D when dw is equal to 0.07 mm,
0.55 D≦n≦1.20 D when dw is equal to 0.08 mm,
0.49 D≦n≦1.06 D when dw is equal to 0.09 mm,
0.44 D≦n≦0.96 D when dw is equal to 0.10 mm, and
0.37 D≦n≦0.80 D when dw is equal to 0.12 mm, wherein "dw" represents a diameter of a strand of each strand bundle in said plurality of strand bundles and "D" represents an average diameter of said netted tube;

wherein K=(S-s)/S, wherein "S" is an area of an intersection of two strand bundles in union with an area of a gap between said intersecting strand bundles and neighboring strand bundles of one side of said intersecting strand bundles, the widths of said area "S" being substantially equal; and wherein "s" is the area of the gap produced by the intersecting strand bundles, wherein no strands are covered, the widths of said area "s" being substantially equal.

64. The netted tube according to claim 63, wherein a maximum value of said average diameter "D" satisfies all the following relationships:

2.5 mm≦D≦5.5 mm when dw is equal to 0.02 mm,
3.8 mm≦D≦8.2 mm when dw is equal to 0.03 mm,
5.1 mm≦D≦11.0 mm when dw is equal to 0.04 mm,
6.3 mm≦D≦13.7 mm when dw is equal to 0.05 mm,
7.5 mm≦D≦16.4 mm when dw is equal to 0.06 mm,
8.8 mm≦D≦19.3 mm when dw is equal to 0.07 mm,
10.0 mm≦D≦21.8 mm when dw is equal to 0.08 mm,
11.4 mm≦D≦24.4 mm when dw is equal to 0.09 mm,
12.5 mm≦D≦27.2 mm when dw is equal to 0.10 mm, and
15.0 mm≦D≦32.4 mm when dw is equal to 0.12 mm.

65. A netted tube, formed by braiding a plurality of strand bundles each formed by closely arranging a plurality of fine wires in parallel, used in a flexible tube for an endoscope, said flexible tube comprising:

a spiral tube, said netted tube covering an outer surface of said spiral tube; and a jacket made of a flexible synthetic resin which covers an outer surface of said netted tube;

wherein the following relationships are satisfied:

$$45° \leq \alpha \leq 65°,$$

$$0.772 \leq K \leq 0.906$$

and $$n=16,$$

wherein "α" represents a braid angle, "K" represents a braid density, and "n" represents a number of strands contained in one of said plurality of strand bundles, and further wherein said number "n" satisfies all the following relationships:

4.34 D≦n≦9.62 D when dw is equal to 0.02 mm,
2.89 D≦n≦6.41 D when dw is equal to 0.03 mm,
2.17 D≦n≦4.81 D when dw is equal to 0.04 mm,
1.74 D≦n≦3.84 D when dw is equal to 0.05 mm,
1.45 D≦n≦3.20 D when dw is equal to 0.06 mm,
1.24 D≦n≦2.74 D when dw is equal to 0.07 mm,
1.09 D≦n≦2.40 D when dw is equal to 0.08 mm,
0.97 D≦n≦2.13 D when dw is equal to 0.09 mm,
0.87 D≦n≦1.92 D when dw is equal to 0.10 mm, and
0.73 D≦n≦1.60 D when dw is equal to 0.12 mm, wherein "dw" represents a diameter of a strand of each strand bundle in said plurality of strand bundles and "D" represents an average diameter of said netted tube;

wherein K=(S-s)/S;

wherein "S" is an area of an intersection of two strand bundles in union with an area of a gap between said intersecting strand bundles and neighboring strand bundles of one side of said intersecting strand bundles, the widths of said area "S" being equal; and wherein "s" is the area of the gap produced by the intersecting strand bundles, wherein no strands are covered, the widths of said area "s" being equal.

66. The netted tube according to claim 65, wherein a maximum value of said average diameter "D" satisfies the following relationships:

1.25 mm≦D≦2.76 mm when dw is equal to 0.02 mm,
1.88 mm≦D≦4.15 mm when dw is equal to 0.03 mm,
2.5 mm≦D≦5.5 mm when dw is equal to 0.04 mm,
3.2 mm≦D≦6.8 mm when dw is equal to 0.05 mm,
3.8 mm≦D≦8.2 mm when dw is equal to 0.06 mm,
4.4 mm≦D≦9.6 mm when dw is equal to 0.07 mm,
5 mm≦D≦11 mm when dw is equal to 0.08 mm,
5.7 mm≦D≦12.3 mm when dw is equal to 0.09 mm,
6.3 mm≦D≦13.7 mm when dw is equal to 0.10 mm, and
7.5 mm≦D≦16.4 mm when dw is equal to 0.12 mm.

67. A netted tube, formed by braiding a plurality of strand bundles each formed by closely arranging a plurality of fine wires in parallel, used in a flexible tube for an endoscope, said flexible tube comprising:

a spiral tube, said netted tube covering an outer surface of said spiral tube; and a jacket made of a flexible synthetic resin which covers an outer surface of said netted tube;

wherein the following relationships are satisfied:

$$45° \leq \alpha \leq 65°,$$

$$0.772 \leq K \leq 0.906$$

and $$n=8,$$

wherein "α" represents a braid angle, "K" represents a braid density, and "n" represents a number of strands contained in one of said plurality of strand bundles, and further wherein said number "n" satisfies all the following relationships:

8.67 D≦n≦19.24 D when dw is equal to 0.02 mm,
5.78 D≦n≦12.82 D when dw is equal to 0.03 mm,
4.34 D≦n≦9.62 D when dw is equal to 0.04 mm,
3.47 D≦n≦7.69 D when dw is equal to 0.05 mm,
2.89 D≦n≦6.41 D when dw is equal to 0.06 mm,
2.48 D≦n≦5.49 D when dw is equal to 0.07 mm, and
2.17 D≦n≦4.81 D when dw is equal to 0.08 mm, wherein "dw" represents a diameter of a strand of each strand bundle in said plurality of strand bundles and "D" represents an average diameter of said netted tubes;

wherein K=(S−s)/S;

wherein "S" is an area of an intersection of two strand bundles in union with an area of a gap between said intersecting strand bundles and neighboring strand bundles of one side of said intersecting strand bundles, the widths of said area "S" being substantially equal; and wherein "s" is the area of the gap produced by the intersecting strand bundles, wherein no strands are covered, the widths of said area "s" being substantially equal.

68. The netted tube according to claim 67, wherein a maximum value of said average diameter "D" satisfies all the following relationships:

$D \leq 1.38$ mm when dw is equal to 0.02 mm,
$D \leq 2.07$ mm when dw is equal to 0.03 mm,
$D \leq 2.76$ mm when dw is equal to 0.04 mm,
$D \leq 3.45$ mm when dw is equal to 0.05 mm,
$D \leq 4.15$ mm when dw is equal to 0.06 mm,
$D \leq 4.83$ mm when dw is equal to 0.07 mm, and
$D \leq 5.52$ mm when dw is equal to 0.08 mm.

* * * * *